United States Patent
Amorese et al.

(10) Patent No.: US 11,725,241 B2
(45) Date of Patent: Aug. 15, 2023

(54) COMPOSITIONS AND METHODS FOR IDENTIFICATION OF A DUPLICATE SEQUENCING READ

(71) Applicant: Tecan Genomics, Inc., Redwood City, CA (US)

(72) Inventors: Douglas A. Amorese, Los Altos, CA (US); Jonathan Scolnick, San Francisco, CA (US); Ben Schroeder, San Mateo, CA (US)

(73) Assignee: Tecan Genomics, Inc., Redwood City, CA (US)

( * ) Notice: Subject to any disclaimer, the term of this patent is extended or adjusted under 35 U.S.C. 154(b) by 187 days.

(21) Appl. No.: 17/381,888

(22) Filed: Jul. 21, 2021

(65) Prior Publication Data

US 2021/0355537 A1 Nov. 18, 2021

Related U.S. Application Data

(60) Continuation of application No. 16/743,604, filed on Jan. 15, 2020, now Pat. No. 11,098,357, which is a continuation of application No. 15/406,002, filed on Jan. 13, 2017, now Pat. No. 10,570,448, which is a division of application No. 14/540,917, filed on Nov. 13, 2014, now Pat. No. 9,546,399.

(60) Provisional application No. 61/903,826, filed on Nov. 13, 2013.

(51) Int. Cl.
*C12Q 1/6874* (2018.01)
*C12Q 1/6869* (2018.01)

(52) U.S. Cl.
CPC ......... *C12Q 1/6874* (2013.01); *C12Q 1/6869* (2013.01); *C12Q 2525/179* (2013.01); *C12Q 2525/191* (2013.01)

(58) Field of Classification Search
CPC ............ C12Q 1/6869; C12Q 2525/191; C12Q 2525/179
See application file for complete search history.

(56) References Cited

U.S. PATENT DOCUMENTS

| | | |
|---|---|---|
| 4,362,867 A | 12/1982 | Paddock |
| 4,458,066 A | 7/1984 | Caruthers et al. |
| 4,469,863 A | 9/1984 | Ts'o et al. |
| 4,582,877 A | 4/1986 | Fairchok et al. |
| 4,876,187 A | 10/1989 | Duck et al. |
| 4,925,065 A | 5/1990 | Golias |
| 4,935,357 A | 6/1990 | Szybalski |
| 4,942,124 A | 7/1990 | Church |
| 4,988,617 A | 1/1991 | Landegren et al. |
| 4,996,143 A | 2/1991 | Heller et al. |
| 5,011,769 A | 4/1991 | Duck et al. |
| 5,034,506 A | 7/1991 | Summerton et al. |
| 5,035,996 A | 7/1991 | Hartley |
| 5,043,272 A | 8/1991 | Hartley |
| 5,082,830 A | 1/1992 | Brakel et al. |
| 5,090,591 A | 2/1992 | Long |
| 5,130,238 A | 7/1992 | Malek et al. |
| 5,169,766 A | 12/1992 | Schuster et al. |
| 5,171,534 A | 12/1992 | Smith et al. |
| 5,194,370 A | 3/1993 | Berninger et al. |
| 5,216,141 A | 6/1993 | Benner |
| 5,234,809 A | 8/1993 | Boom et al. |
| 5,235,033 A | 8/1993 | Summerton et al. |
| 5,242,794 A | 9/1993 | Whiteley et al. |
| 5,384,242 A | 1/1995 | Oakes |
| 5,386,023 A | 1/1995 | Sanghvi et al. |
| 5,399,491 A | 3/1995 | Kacian et al. |
| 5,409,818 A | 4/1995 | Davey et al. |
| 5,418,149 A | 5/1995 | Gelfand et al. |
| 5,422,271 A | 6/1995 | Chen et al. |
| 5,427,929 A | 6/1995 | Richards et al. |
| 5,480,784 A | 1/1996 | Kacian et al. |
| 5,494,810 A | 2/1996 | Barany et al. |
| 5,508,169 A | 4/1996 | Deugau et al. |
| 5,508,178 A | 4/1996 | Rose et al. |
| 5,510,270 A | 4/1996 | Fodor et al. |
| 5,525,471 A | 6/1996 | Zeng |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,565,340 A | 10/1996 | Chenchik et al. |
| 5,573,913 A | 11/1996 | Rosemeyer et al. |
| 5,578,832 A | 11/1996 | Trulson et al. |
| 5,589,339 A | 12/1996 | Hampson et al. |
| 5,602,240 A | 2/1997 | De Mesmaeker et al. |

(Continued)

FOREIGN PATENT DOCUMENTS

| | | |
|---|---|---|
| CA | 2444926 A1 | 11/2002 |
| CN | 1661102 A | 8/2005 |

(Continued)

OTHER PUBLICATIONS

Kinde, I. et al., Detection and quantification of rare mutations with massively parallel sequencing, PNAS, vol. 108, pp. 9530-9535, 2011) (Year: 2011).*
Wolford, 2000, High-throughput SNP detection by using DNA pooling and denaturing high performance liquid chromatography (DHPLC), Hum Genet 107:483-487.
Xi, 2011, Copy number variation detection in whole-genome sequencing data using the Bayesian information criterion, PNAS 108(46):e1128-e1136.
Xu, 2012, FastUniq: A fast de novo duplicates removal tool for paired short reads, PLoSOne 7(12):e52249.

(Continued)

*Primary Examiner* — Teresa E Strzelecka
(74) *Attorney, Agent, or Firm* — Brown Rudnick LLP; Adam M. Schoen

(57) ABSTRACT

The present invention provides methods, compositions and kits for detecting duplicate sequencing reads. In some embodiments, the duplicate sequencing reads are removed.

16 Claims, 6 Drawing Sheets
Specification includes a Sequence Listing.

(56) References Cited

U.S. PATENT DOCUMENTS

| | | |
|---|---|---|
| 5,637,684 A | 6/1997 | Cook et al. |
| 5,641,658 A | 6/1997 | Adams et al. |
| 5,644,048 A | 7/1997 | Yau |
| 5,665,549 A | 9/1997 | Pinkel et al. |
| 5,667,976 A | 9/1997 | Van Ness et al. |
| 5,667,979 A | 9/1997 | Berrens |
| 5,679,512 A | 10/1997 | Laney et al. |
| 5,681,726 A | 10/1997 | Huse et al. |
| 5,683,879 A | 11/1997 | Laney et al. |
| 5,688,648 A | 11/1997 | Mathies et al. |
| 5,705,628 A | 1/1998 | Hawkins |
| 5,708,154 A | 1/1998 | Smith et al. |
| 5,710,028 A | 1/1998 | Eyal et al. |
| 5,712,126 A | 1/1998 | Weissman et al. |
| 5,716,785 A | 2/1998 | Van Gelder et al. |
| 5,726,329 A | 3/1998 | Jones et al. |
| 5,750,341 A | 5/1998 | Macevicz |
| 5,759,822 A | 6/1998 | Chenchik et al. |
| 5,763,178 A | 6/1998 | Chirikjian et al. |
| 5,789,206 A | 8/1998 | Tavtigian et al. |
| 5,824,517 A | 10/1998 | Cleuziat et al. |
| 5,824,518 A | 10/1998 | Kacian et al. |
| 5,837,832 A | 11/1998 | Chee et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,945,313 A | 8/1999 | Hartley et al. |
| 5,952,176 A | 9/1999 | McCarthy et al. |
| 5,958,681 A | 9/1999 | Wetmur et al. |
| 5,965,409 A | 10/1999 | Pardee et al. |
| 5,969,119 A | 10/1999 | Macevicz |
| 5,972,618 A | 10/1999 | Bloch |
| 6,004,744 A | 12/1999 | Goelet et al. |
| 6,004,745 A | 12/1999 | Arnold, Jr. et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,056,661 A | 5/2000 | Schmidt |
| 6,077,674 A | 6/2000 | Schleifer et al. |
| 6,087,103 A | 7/2000 | Burmer |
| 6,090,553 A | 7/2000 | Matson |
| 6,090,591 A | 7/2000 | Burg et al. |
| 6,107,023 A | 8/2000 | Reyes et al. |
| 6,110,709 A | 8/2000 | Ausubel et al. |
| 6,150,112 A | 11/2000 | Weissman et al. |
| 6,159,685 A | 12/2000 | Pinkel et al. |
| 6,160,105 A | 12/2000 | Cunningham et al. |
| 6,169,194 B1 | 1/2001 | Thompson et al. |
| 6,172,208 B1 | 1/2001 | Cook |
| 6,174,680 B1 | 1/2001 | Makrigiorgos |
| 6,180,338 B1 | 1/2001 | Adams |
| 6,190,865 B1 | 2/2001 | Jendrisak et al. |
| 6,194,211 B1 | 2/2001 | Richards et al. |
| 6,197,501 B1 | 3/2001 | Cremer et al. |
| 6,197,557 B1 | 3/2001 | Makarov et al. |
| 6,210,891 B1 | 4/2001 | Nyren et al. |
| 6,225,109 B1 | 5/2001 | Juncosa et al. |
| 6,225,451 B1 | 5/2001 | Ballinger et al. |
| 6,232,104 B1 | 5/2001 | Lishanski et al. |
| 6,251,639 B1 | 6/2001 | Kurn |
| 6,262,490 B1 | 7/2001 | Hsu et al. |
| 6,270,961 B1 | 8/2001 | Drmanac |
| 6,280,935 B1 | 8/2001 | Macevicz |
| 6,287,766 B1 | 9/2001 | Nolan et al. |
| 6,287,825 B1 | 9/2001 | Weissman et al. |
| 6,291,170 B1 | 9/2001 | Van Gelder et al. |
| 6,306,365 B1 | 10/2001 | Ruoslahti et al. |
| 6,306,597 B1 | 10/2001 | Macevicz |
| 6,309,843 B1 | 10/2001 | Timms |
| 6,326,142 B1 | 12/2001 | Royer |
| 6,335,167 B1 | 1/2002 | Pinkel et al. |
| 6,339,147 B1 | 1/2002 | Lukhtanov et al. |
| 6,440,705 B1 | 8/2002 | Stanton, Jr. et al. |
| 6,449,562 B1 | 9/2002 | Chandler et al. |
| 6,582,938 B1 | 6/2003 | Su et al. |
| 6,670,461 B1 | 12/2003 | Wengel et al. |
| 6,686,156 B2 | 2/2004 | Kurn |
| 6,692,918 B2 | 2/2004 | Kurn |
| 6,770,748 B2 | 8/2004 | Imanishi et al. |
| 6,777,180 B1 | 8/2004 | Fisher et al. |
| 6,794,499 B2 | 9/2004 | Wengel et al. |
| 6,815,164 B2 | 11/2004 | Kurn |
| 6,815,167 B2 | 11/2004 | Crothers et al. |
| 6,825,011 B1 | 11/2004 | Romantchikov |
| 6,833,246 B2 | 12/2004 | Balasubramanian |
| 6,849,404 B2 | 2/2005 | Park et al. |
| 6,858,413 B2 | 2/2005 | Kurn |
| 6,913,884 B2 | 7/2005 | Stuelpnagel et al. |
| 6,917,726 B2 | 7/2005 | Levene et al. |
| 6,924,104 B2 | 8/2005 | Weissman et al. |
| 6,946,251 B2 | 9/2005 | Kurn |
| 7,001,724 B1 | 2/2006 | Greenfield |
| 7,033,764 B2 | 4/2006 | Korlach et al. |
| 7,048,481 B2 | 5/2006 | Sugata et al. |
| 7,052,847 B2 | 5/2006 | Korlach et al. |
| 7,056,676 B2 | 6/2006 | Korlach et al. |
| 7,056,716 B2 | 6/2006 | Potter et al. |
| 7,060,441 B2 | 6/2006 | Bourget et al. |
| 7,094,536 B2 | 8/2006 | Kurn |
| 7,115,400 B1 | 10/2006 | Adessi et al. |
| 7,170,050 B2 | 1/2007 | Turner et al. |
| 7,175,982 B1 | 2/2007 | McCarthy et al. |
| 7,176,025 B2 | 2/2007 | Kurn et al. |
| 7,189,512 B2 | 3/2007 | Porat et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,273,730 B2 | 9/2007 | Du Breuil Lastrucci |
| 7,276,720 B2 | 10/2007 | Ulmer |
| 7,294,461 B2 | 11/2007 | Kurn |
| 7,300,755 B1 | 11/2007 | Petersdorf et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,351,557 B2 | 4/2008 | Kurn |
| 7,354,717 B2 | 4/2008 | Kurn |
| 7,361,466 B2 | 4/2008 | Korlach et al. |
| 7,361,468 B2 | 4/2008 | Liu et al. |
| 7,402,386 B2 | 7/2008 | Kurn et al. |
| 7,405,281 B2 | 7/2008 | Xu et al. |
| 7,414,117 B2 | 8/2008 | Saito et al. |
| 7,416,844 B2 | 8/2008 | Korlach et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 7,579,153 B2 | 8/2009 | Brenner et al. |
| 7,704,687 B2 | 4/2010 | Wang et al. |
| 7,741,463 B2 | 6/2010 | Gormley et al. |
| 7,771,934 B2 | 8/2010 | Kurn |
| 7,771,946 B2 | 8/2010 | Kurn |
| 7,803,550 B2 | 9/2010 | Makarov et al. |
| 7,846,666 B2 | 12/2010 | Kurn |
| 7,846,733 B2 | 12/2010 | Kurn |
| 7,867,703 B2 | 1/2011 | Sampson et al. |
| 7,939,258 B2 | 5/2011 | Kurn et al. |
| 7,948,015 B2 | 5/2011 | Rothberg et al. |
| 7,985,565 B2 | 7/2011 | Mayer et al. |
| 8,017,335 B2 | 9/2011 | Smith |
| 8,034,568 B2 | 10/2011 | Kurn et al. |
| 8,053,192 B2 | 11/2011 | Bignell et al. |
| 8,071,311 B2 | 12/2011 | Kurn |
| 8,143,001 B2 | 3/2012 | Kurn et al. |
| 8,209,130 B1 | 6/2012 | Kennedy et al. |
| 8,334,116 B2 | 12/2012 | Kurn |
| 8,465,950 B2 | 6/2013 | Kurn et al. |

(56) References Cited

U.S. PATENT DOCUMENTS

| | | |
|---|---|---|
| 8,492,095 B2 | 7/2013 | Kurn |
| 8,512,956 B2 | 8/2013 | Kurn |
| 8,551,709 B2 | 10/2013 | Kurn et al. |
| 8,852,867 B2 | 10/2014 | Kurn et al. |
| 8,999,677 B1 | 4/2015 | Soldatov et al. |
| 9,175,325 B2 | 11/2015 | Kurn et al. |
| 9,175,336 B2 | 11/2015 | Soldatov et al. |
| 9,181,582 B2 | 11/2015 | Kurn |
| 9,206,418 B2 | 12/2015 | Armour |
| 9,248,076 B2 | 2/2016 | Sullivan et al. |
| 9,546,399 B2 | 1/2017 | Amorese et al. |
| 9,702,004 B2 | 7/2017 | Van Eijk et al. |
| 9,745,627 B2 | 8/2017 | Van Eijk et al. |
| 9,896,721 B2 | 2/2018 | van Eijk et al. |
| 2001/0000077 A1 | 3/2001 | Engelhardt et al. |
| 2001/0031739 A1 | 10/2001 | Dare |
| 2001/0034048 A1 | 10/2001 | Kurn |
| 2001/0041334 A1 | 11/2001 | Rashtchian et al. |
| 2002/0028447 A1 | 3/2002 | Li et al. |
| 2002/0058270 A1 | 5/2002 | Kurn |
| 2002/0115088 A1 | 8/2002 | Kurn |
| 2002/0150919 A1 | 10/2002 | Weismann et al. |
| 2002/0155451 A1 | 10/2002 | Makrigiorgos |
| 2002/0164628 A1 | 11/2002 | Kurn |
| 2002/0164634 A1 | 11/2002 | Patil et al. |
| 2002/0197639 A1 | 12/2002 | Shia et al. |
| 2003/0017591 A1 | 1/2003 | Kurn |
| 2003/0022207 A1 | 1/2003 | Balasubramanian et al. |
| 2003/0082543 A1 | 5/2003 | Su et al. |
| 2003/0087251 A1 | 5/2003 | Kurn |
| 2003/0119150 A1 | 6/2003 | Ankenbauer et al. |
| 2003/0143555 A1 | 7/2003 | Bourget et al. |
| 2003/0175780 A1 | 9/2003 | Jones |
| 2003/0180779 A1 | 9/2003 | Lofton-Day et al. |
| 2003/0186234 A1 | 10/2003 | Kurn |
| 2003/0207279 A1 | 11/2003 | Crothers et al. |
| 2003/0211616 A1 | 11/2003 | Leong |
| 2003/0215926 A1 | 11/2003 | Kurn et al. |
| 2003/0224439 A1 | 12/2003 | Lafferty et al. |
| 2003/0232348 A1 | 12/2003 | Jones et al. |
| 2004/0002371 A1 | 1/2004 | Paquin et al. |
| 2004/0005614 A1 | 1/2004 | Kurn et al. |
| 2004/0023271 A1 | 2/2004 | Kurn et al. |
| 2004/0115815 A1 | 6/2004 | Li et al. |
| 2004/0137456 A1 | 7/2004 | Yokota et al. |
| 2004/0161742 A1 | 8/2004 | Dean et al. |
| 2004/0203019 A1 | 10/2004 | Kurn |
| 2004/0203025 A1 | 10/2004 | Kurn |
| 2004/0248153 A1 | 12/2004 | Dear et al. |
| 2005/0003441 A1 | 1/2005 | Kurn |
| 2005/0014192 A1 | 1/2005 | Kurn |
| 2005/0019793 A1 | 1/2005 | Kurn et al. |
| 2005/0059048 A1 | 3/2005 | Gunderson et al. |
| 2005/0064456 A1 | 3/2005 | Kurn |
| 2005/0123956 A1 | 6/2005 | Blume et al. |
| 2005/0136417 A1 | 6/2005 | Cole et al. |
| 2005/0142577 A1 | 6/2005 | Jones et al. |
| 2005/0191656 A1 | 9/2005 | Drmanac et al. |
| 2005/0191682 A1 | 9/2005 | Barone et al. |
| 2005/0208538 A1 | 9/2005 | Kurn et al. |
| 2006/0008824 A1 | 1/2006 | Ronaghi et al. |
| 2006/0014182 A1 | 1/2006 | Kurn |
| 2006/0024678 A1 | 2/2006 | Buzby |
| 2006/0024711 A1 | 2/2006 | Lapidus et al. |
| 2006/0035274 A1 | 2/2006 | Dong |
| 2006/0046251 A1 | 3/2006 | Sampson et al. |
| 2006/0051789 A1 | 3/2006 | Kazakov et al. |
| 2006/0068415 A1 | 3/2006 | Jones et al. |
| 2006/0134633 A1 | 6/2006 | Chen et al. |
| 2006/0216724 A1 | 9/2006 | Christians et al. |
| 2006/0263789 A1 | 11/2006 | Kincaid |
| 2006/0281082 A1 | 12/2006 | Zhu |
| 2006/0286566 A1 | 12/2006 | Lapidus et al. |
| 2006/0292597 A1 | 12/2006 | Shapero et al. |
| 2007/0031857 A1 | 2/2007 | Makarov et al. |
| 2007/0134128 A1 | 6/2007 | Korlach |
| 2007/0141604 A1 | 6/2007 | Gormley et al. |
| 2007/0224607 A1 | 9/2007 | Morgan et al. |
| 2007/0224613 A1 | 9/2007 | Strathmann |
| 2007/0231823 A1 | 10/2007 | McKernan et al. |
| 2007/0238122 A1 | 10/2007 | Allbritton et al. |
| 2007/0263045 A1 | 11/2007 | Okazawa |
| 2008/0038727 A1 | 2/2008 | Spier |
| 2008/0087826 A1 | 4/2008 | Harris et al. |
| 2008/0103058 A1 | 5/2008 | Siddiqi |
| 2008/0131937 A1 | 6/2008 | Schroeder |
| 2008/0160580 A1 | 7/2008 | Adessi et al. |
| 2008/0176311 A1 | 7/2008 | Kurn |
| 2008/0182300 A1 | 7/2008 | Kurn |
| 2008/0194413 A1 | 8/2008 | Albert |
| 2008/0194416 A1 | 8/2008 | Chen |
| 2008/0206764 A1 | 8/2008 | Williams et al. |
| 2008/0213770 A1 | 9/2008 | Williams et al. |
| 2008/0217246 A1 | 9/2008 | Benn et al. |
| 2008/0241831 A1 | 10/2008 | Fan et al. |
| 2008/0242560 A1 | 10/2008 | Gunderson et al. |
| 2008/0286795 A1 | 11/2008 | Kawashima et al. |
| 2009/0011959 A1 | 1/2009 | Costa et al. |
| 2009/0024331 A1 | 1/2009 | Tomaney et al. |
| 2009/0026082 A1 | 1/2009 | Rothberg et al. |
| 2009/0029385 A1 | 1/2009 | Christians et al. |
| 2009/0036663 A1 | 2/2009 | Kurn |
| 2009/0061425 A1 | 3/2009 | Lo et al. |
| 2009/0061439 A1 | 3/2009 | Buzby |
| 2009/0068645 A1 | 3/2009 | Sibson |
| 2009/0068655 A1 | 3/2009 | Williams |
| 2009/0068709 A1 | 3/2009 | Kurn et al. |
| 2009/0105081 A1 | 4/2009 | Rodesch et al. |
| 2009/0117573 A1 | 5/2009 | Fu et al. |
| 2009/0117621 A1 | 5/2009 | Boutell et al. |
| 2009/0124514 A1 | 5/2009 | Fu et al. |
| 2009/0127589 A1 | 5/2009 | Rothberg et al. |
| 2009/0130721 A1 | 5/2009 | Kurn et al. |
| 2009/0203085 A1 | 8/2009 | Kurn et al. |
| 2009/0203531 A1 | 8/2009 | Kurn |
| 2009/0233802 A1 | 9/2009 | Bignell et al. |
| 2009/0233804 A1 | 9/2009 | Kurn et al. |
| 2009/0239232 A1 | 9/2009 | Kurn |
| 2009/0275486 A1 | 11/2009 | Kurn et al. |
| 2009/0280538 A1 | 11/2009 | Patel et al. |
| 2009/0298075 A1 | 12/2009 | Travers et al. |
| 2010/0015666 A1 | 1/2010 | Brenner et al. |
| 2010/0021973 A1 | 1/2010 | Makarov et al. |
| 2010/0022403 A1 | 1/2010 | Kurn et al. |
| 2010/0029511 A1 | 2/2010 | Raymond et al. |
| 2010/0105052 A1 | 4/2010 | Drmanac et al. |
| 2010/0113296 A1 | 5/2010 | Myerson |
| 2010/0129879 A1 | 5/2010 | Ach et al. |
| 2010/0137143 A1 | 6/2010 | Rothberg et al. |
| 2010/0159559 A1 | 6/2010 | Kurn et al. |
| 2010/0167954 A1 | 7/2010 | Earnshaw et al. |
| 2010/0173394 A1 | 7/2010 | Colston, Jr. et al. |
| 2010/0203597 A1 | 8/2010 | Chen et al. |
| 2010/0267043 A1 | 10/2010 | Braverman et al. |
| 2010/0273219 A1 | 10/2010 | May et al. |
| 2010/0311066 A1 | 12/2010 | Kurn |
| 2010/0323348 A1 | 12/2010 | Hamady et al. |
| 2011/0015096 A1 | 1/2011 | Chiu |
| 2011/0039732 A1 | 2/2011 | Raymond et al. |
| 2011/0104785 A1 | 5/2011 | Vaidyanathan et al. |
| 2011/0105364 A1 | 5/2011 | Kurn |
| 2011/0129827 A1 | 6/2011 | Causey et al. |
| 2011/0189679 A1 | 8/2011 | Kurn et al. |
| 2011/0224105 A1 | 9/2011 | Kurn et al. |
| 2011/0269647 A1 | 11/2011 | Ule et al. |
| 2011/0288780 A1 | 11/2011 | Rabinowitz et al. |
| 2011/0294132 A1 | 12/2011 | Kurn |
| 2011/0319290 A1 | 12/2011 | Raymond et al. |
| 2012/0003657 A1 | 1/2012 | Myllykangas et al. |
| 2012/0028310 A1 | 2/2012 | Kurn et al. |
| 2012/0045797 A1 | 2/2012 | Kurn et al. |
| 2012/0071331 A1 | 3/2012 | Casbon et al. |
| 2012/0074925 A1 | 3/2012 | Oliver |
| 2012/0102054 A1 | 4/2012 | Popescu et al. |

(56) References Cited

U.S. PATENT DOCUMENTS

| | | |
|---|---|---|
| 2012/0107811 A1 | 5/2012 | Kelso et al. |
| 2012/0122701 A1 | 5/2012 | Ryan et al. |
| 2012/0149068 A1 | 6/2012 | Kurn |
| 2012/0156728 A1 | 6/2012 | Li et al. |
| 2012/0157322 A1 | 6/2012 | Myllykangas et al. |
| 2012/0190587 A1 | 7/2012 | Kurn et al. |
| 2012/0208705 A1 | 8/2012 | Steemers et al. |
| 2012/0220483 A1 | 8/2012 | Kurn et al. |
| 2012/0220494 A1 | 8/2012 | Samuels et al. |
| 2012/0237943 A1 | 9/2012 | Soldatov et al. |
| 2012/0238738 A1 | 9/2012 | Hendrickson |
| 2012/0245041 A1 | 9/2012 | Brenner et al. |
| 2012/0270212 A1 | 10/2012 | Rabinowitz et al. |
| 2012/0283145 A1 | 11/2012 | Wang |
| 2012/0289426 A1 | 11/2012 | Roos et al. |
| 2012/0309002 A1 | 12/2012 | Link |
| 2013/0005585 A1 | 1/2013 | Anderson et al. |
| 2013/0059738 A1 | 3/2013 | Leamon et al. |
| 2013/0231253 A1 | 9/2013 | Amorese et al. |
| 2014/0038188 A1 | 2/2014 | Kurn |
| 2014/0038236 A1 | 2/2014 | Kurn et al. |
| 2014/0065692 A1 | 3/2014 | Kurn et al. |
| 2014/0274729 A1 | 9/2014 | Kurn et al. |
| 2014/0274731 A1 | 9/2014 | Raymond et al. |
| 2014/0274738 A1 | 9/2014 | Amorese et al. |
| 2014/0303000 A1 | 10/2014 | Armour |
| 2014/0378345 A1 | 12/2014 | Hindson et al. |
| 2015/0011396 A1 | 1/2015 | Schroeder et al. |
| 2015/0017635 A1 | 1/2015 | Myllykangas et al. |
| 2015/0101595 A1 | 4/2015 | Hancock et al. |
| 2015/0133319 A1 | 5/2015 | Fu et al. |
| 2015/0284769 A1 | 10/2015 | Schroeder |
| 2015/0299767 A1 | 10/2015 | Armour et al. |
| 2015/0299784 A1 | 10/2015 | Fan et al. |
| 2015/0299812 A1 | 10/2015 | Talasaz |
| 2016/0122756 A1 | 5/2016 | Armour |
| 2016/0130576 A1 | 5/2016 | Armour |
| 2016/0153039 A1 | 6/2016 | Amorese et al. |
| 2016/0203259 A1 | 7/2016 | Scolnick et al. |
| 2016/0220994 A1 | 8/2016 | Wright |
| 2016/0251711 A1 | 9/2016 | Amorese et al. |
| 2016/0265042 A1 | 9/2016 | Schroeder et al. |
| 2016/0275240 A1 | 9/2016 | Huelga et al. |
| 2016/0296930 A1 | 10/2016 | Matear et al. |
| 2022/0145380 A1* | 5/2022 | Doan ................. C12Q 1/6851 |

FOREIGN PATENT DOCUMENTS

| | | | |
|---|---|---|---|
| CN | 101565746 A | | 10/2009 |
| CN | 105890722 A | | 8/2016 |
| EP | 0365627 B1 | | 12/1993 |
| EP | 0329822 B1 | | 6/1994 |
| EP | 0667393 A2 | | 8/1995 |
| EP | 1071811 B1 | | 3/2002 |
| EP | 0843735 B1 | | 7/2002 |
| EP | 2272976 A1 | | 1/2011 |
| EP | 2322612 A1 | | 5/2011 |
| EP | 2451973 A1 | | 5/2012 |
| EP | 2511381 A1 | | 10/2012 |
| EP | 1929039 B2 | | 11/2013 |
| WO | 89/09284 A1 | | 10/1989 |
| WO | 92/07951 A1 | | 5/1992 |
| WO | 93/18052 A1 | | 9/1993 |
| WO | 94/16090 A1 | | 7/1994 |
| WO | 96/40998 A1 | | 12/1996 |
| WO | 97/12061 A1 | | 4/1997 |
| WO | 97/25416 A2 | | 7/1997 |
| WO | 98/06736 A1 | | 2/1998 |
| WO | 98/38296 A1 | | 9/1998 |
| WO | 98/044151 A1 | | 10/1998 |
| WO | 99/10540 A1 | | 3/1999 |
| WO | 99/11819 A1 | | 3/1999 |
| WO | 99/42618 A1 | | 8/1999 |
| WO | 00/08208 A2 | | 2/2000 |
| WO | 2000/09756 A1 | | 2/2000 |
| WO | 00/018957 A1 | | 4/2000 |
| WO | 00/39345 A1 | | 7/2000 |
| WO | 00/52191 A1 | | 9/2000 |
| WO | 2000/55364 A2 | | 9/2000 |
| WO | 00/70039 A1 | | 11/2000 |
| WO | 01/20035 A2 | | 3/2001 |
| WO | 01/23613 A1 | | 4/2001 |
| WO | 01/46464 A1 | | 6/2001 |
| WO | 01/57248 A2 | | 8/2001 |
| WO | 01/64952 A2 | | 9/2001 |
| WO | 02/00938 A2 | | 1/2002 |
| WO | 02/28876 A2 | | 4/2002 |
| WO | 02/29117 A2 | | 4/2002 |
| WO | 02/36821 A2 | | 5/2002 |
| WO | 02/48402 A2 | | 6/2002 |
| WO | 02/060318 A2 | | 8/2002 |
| WO | 02/072772 A2 | | 9/2002 |
| WO | 02/072773 A2 | | 9/2002 |
| WO | 02/081753 A1 | | 10/2002 |
| WO | 02/090584 A2 | | 11/2002 |
| WO | 03/004690 A2 | | 1/2003 |
| WO | 2003/002736 A2 | | 1/2003 |
| WO | 2003/012118 A1 | | 2/2003 |
| WO | 03/027259 A2 | | 4/2003 |
| WO | 03/078645 A2 | | 9/2003 |
| WO | 03/083435 A2 | | 10/2003 |
| WO | 03/106642 A2 | | 12/2003 |
| WO | 04/011665 A2 | | 2/2004 |
| WO | 2004/070007 A2 | | 8/2004 |
| WO | 2004/092418 A2 | | 10/2004 |
| WO | 2005/003375 A2 | | 1/2005 |
| WO | 2005/038427 A2 | | 4/2005 |
| WO | 2005/065321 A2 | | 7/2005 |
| WO | 2006/081222 A2 | | 8/2006 |
| WO | 2006/086668 A2 | | 8/2006 |
| WO | 2006/137733 A1 | | 12/2006 |
| WO | 2007/018601 A1 | | 2/2007 |
| WO | 2007/019444 A2 | | 2/2007 |
| WO | 2007/030759 A2 | | 3/2007 |
| WO | 2007/037678 A2 | | 4/2007 |
| WO | 2007/052006 A1 | | 5/2007 |
| WO | 2007/057652 A1 | | 5/2007 |
| WO | 2007/073165 A1 | | 6/2007 |
| WO | 2007/136717 A1 | | 11/2007 |
| WO | 2008/005459 A2 | | 1/2008 |
| WO | 2008/015396 A2 | | 2/2008 |
| WO | 2008/033442 A2 | | 3/2008 |
| WO | 2008/093098 A2 | | 8/2008 |
| WO | 2008/115185 A2 | | 9/2008 |
| WO | 2008150432 A1 | | 12/2008 |
| WO | 2009/053039 A1 | | 4/2009 |
| WO | 2009/102878 A2 | | 8/2009 |
| WO | 2009/102896 A2 | | 8/2009 |
| WO | 2009/112844 A1 | | 9/2009 |
| WO | 2009/117698 A2 | | 9/2009 |
| WO | 2009/120372 A2 | | 10/2009 |
| WO | 2009/120374 A2 | | 10/2009 |
| WO | 2010/003153 A2 | | 1/2010 |
| WO | 2010/030683 A1 | | 3/2010 |
| WO | 2010/039991 A2 | | 4/2010 |
| WO | 2010/063711 A1 | | 6/2010 |
| WO | 2010/064893 A1 | | 6/2010 |
| WO | 2010/085715 A1 | | 7/2010 |
| WO | 2010/091246 A2 | | 8/2010 |
| WO | 2010/115154 A1 | | 10/2010 |
| WO | 2010/129937 A2 | | 11/2010 |
| WO | 2011/003630 A1 | | 1/2011 |
| WO | 2011/009941 A1 | | 1/2011 |
| WO | 2011/019964 A1 | | 2/2011 |
| WO | 2011/032053 A1 | | 3/2011 |
| WO | 2011032040 A1 | | 3/2011 |
| WO | 2011/053987 A1 | | 5/2011 |
| WO | 2011/151777 A1 | | 12/2011 |
| WO | 2011/156529 A2 | | 12/2011 |
| WO | 2012/013932 A1 | | 2/2012 |
| WO | 2012/061832 A1 | | 5/2012 |
| WO | 2012/054873 A3 | | 8/2012 |
| WO | 2012/103154 A1 | | 8/2012 |
| WO | 2013/059740 A1 | | 4/2013 |

(56) References Cited

FOREIGN PATENT DOCUMENTS

| WO | 2013/059746 A1 | 4/2013 |
| WO | 2013/112923 A1 | 8/2013 |
| WO | 2013/130512 A3 | 10/2013 |
| WO | 2013/177220 A1 | 11/2013 |
| WO | 2013/190441 A2 | 12/2013 |
| WO | 2013/191775 A2 | 12/2013 |
| WO | 2014/039556 A1 | 3/2014 |
| WO | 2014/082032 A1 | 5/2014 |
| WO | 2013/138510 A9 | 7/2014 |
| WO | 2014/144092 A1 | 9/2014 |
| WO | 2014/150931 A1 | 9/2014 |
| WO | 2015/031691 A1 | 3/2015 |
| WO | 2015/073711 A1 | 5/2015 |
| WO | 2015/131107 A1 | 9/2015 |

OTHER PUBLICATIONS

Amos, 2000, DNA pooling in mutation detection with reference to sequence analysis, Am J Hum Genet 66:1689-1692.
Bellos, 2014, cnvCapSeq: detecting copy number variation in long-range targeted resequencing data, Nucleic Acids Res 42(20):e158.
Benson, 2013, Genbank, Nucl Acids Res 41:D36-D42.
Blomquist, 2013, Targeted RNA-Sequencing with Competitive Multiplex-PCR Amplicon Libraries, PLOS One 8(11): e79120.
Bodi, 2013, Comparison of commercially available target enrichment methods for next-generation sequencing, J Biomolecular Tech 24:73-86.
Church, 1988, Multiplexed DNA sequencing, Science 240:185-188.
Colbert, 2001, High-throughput screening for induced point mutations, Plant Physiol 126:480-484.
Collard, 2005, An introduction to markers, quantitative trait loci (QTL) mapping and marker-assisted selection for crop improvements: the basic concepts Euphytica 142:169-196.
Eminaga, 2013, Quantification of microRNA Expression with Next-Generation Sequencing, Unit 4.17 in Current Protocols in Molecular Biology, Wiley, New York, NY (14 pages).
Fakhrai-Rad, 2002, Pyroseqeuncing: An accurate detection platform for single nucleotide polymorphisms, Human Mutation 19:479-485.
Grothues, 1993, PCR amplification of megabase DNA with tagged random primers (T-PCR), Nucl Acids Res 21:1321-1322.
Hajibabaei, 2005, Critical factors for assembling a high volume of DNA barcodes, Phil Trans R Soc B 360:1959-1967.
Illumina, 2008, Multiplexed Sequencing with the Illumina Genome Analyzer System, Illumina Sequencing, 4 pages.
Illumina, 2011, TruSeq RNA and DNA Sample Preparation Kits v2, 1-15 Illumina, dated Apr. 27, 2011 (4 pages).
Ion Total RNA-Seq Kit v2, User Guide, 2012, Life Technologies (82 pages).
Jiang, 2015, CODEX: a normalization and copy number variation detection method for whole exome sequencing, Nucleic Acids Res 43(6):e39.
Krumm, 2012, Copy number variation detection and genotyping from exome sequence data, Genome Res 22 (8):1525-1532.
Lai, 2004, Characterization of the maize endosperm transcriptome and its comparison to the rice genome, Genome Res14:1932-1937.
Langmead, 2009, Ultrafast and memory-efficient alignment of short DNA sequences to the human genome, Genome Biol 10:R25.
Li, 2012, CONTRA: copy number analysis for targeted resequencing, Bioinformatics 28(10):1307-1313.
Lindstrom, 2004, Pyrosequencing for detection of Lamivudine-resistant Hepatitis B virus, J Clin Microb 42 (10):4788-4795.
Liu, 2008, Sequence space coverage, entropy of genomes and the potential to detect non-human DNA in human samples, BMC Genomics 9(509):1-17.
Ma, 2015, Quantitative Analysis of Copy Number Variants Based on Real-Time LightCycler PCR, Curr Protoc Hum Genet 80:7.21.1-7.23.8.

Machine translation generated on Mar. 7, 2018, of CN 105890722 by website of European Patent Office (4 pages).
Margulies, 2005, Genome sequencing in open microfabricated high density picoliter reactors, Nature 437 (7057):376-380.
McCloskey, 2007, Encoding PCR products with batch-stamps and barcodes, Biochem Genet 45:761-767.
Miner, 2004, Molecular barcodes detect redundancy and contamination in hairpin-bisulfite PCR, Nucl Acids Res 32 (17):e135, 4 pages.
Myers, 2013, Protocol for Creating Multiplexed miRNA Libraries for Use in Illumina Sequencing, Myers lab microRNA-seq Protocol, Hudson Alpha Institute for Biotechnology web site, dated May 2, 2013, (15 pages).
NuGEN, 2014, User Guide Ovation Target Enrichment System, NuGEN Technologies Inc., San Carlos, CA (45 pages).
Plagnol, 2012, A robust model for read count data in exome sequencing experiments and implications for copy number variant calling, Bioinformatics 28(21):2747-2754.
Qiu, 2003, DNA sequence-based "bar-codes" for tracking the origins of expressed sequence tags from a maize cDNA ibrary constructed using multiple mRNA sources, Plant Physiol 133:475-481.
Querfurth, 2012, Creation and application of immortalized bait libraries for targeted enrichment and next-generation sequencing, Biotechniques 52(6):375-380.
Ronaghi, 2001, Pyrosequencing sheds light on DNA sequencing, Genome Res 11:3-11.
Sathirapongsasuti, 2011, Exome sequencing-based copy-number variation and loss of heterozygosity detection: ExomeCNV, Bioinformatics 27(19):2648-2654.
Schiemer, 2011, Illumina TruSeq Adapters Demystified, Tufts University Core Facility XP055357867 (5 pages).
Shapero, 2001, SNP Genotyping by multiplexed solid-phase amplification and fluorescent minisequencing, Genome Res 11:1926-1934.
Shendure, 2005, Accurate multiplex polony sequencing of an evolved bacterial genome, Science 309:1728.
Soni, 2007, Progress toward ultrafast DNA sequencing using solid-state nanopores, Clin Chem 53(11):1996-2001.
Sood, 2006, Methods for reverse genetic screening in zebrafish by resequencing and Tilling, Methods 39:220-227.
Staroscik, 2004, Calculator for determining the number of copies of a template, URI Genomics, webpage archive dated Apr. 6, 2017 (1 page), Retreived from the internet on Mar. 7, 2018, from <https://web.archive.org/web/20170406174850/http://cels.uri.edu/gsc/cndna.html>.
Stratagene, 1998, Gene characterization kits, Stratagene Catalog, p. 39 (2 pages).
Till, 2003, Large-scale discovery of induced point mutations with high-throughput Tilling, Genome Res 13:524-530.
Trapnell, 2010, Transcript assembly and quantification by RNA-Seq reveals unannotated transcripts and isoform switching during cell differentiation, Nat Biotech 28:511-515.
Trapnell, 2013, Differential analysis of gene regulation at transcript resolution with RNA-seq, Nat Biotech 31:46-53.
Unemo, 2004, Molecular typing of Neisseria gonorrhoeae isolates by pyrosequencing of highly polymorphic segments of the porB gene, J Clin Microb 42(7):2926-2934.
Vasil, 2012, Next generation sequencing for molecular diagnosis of neuromuscular diseases, Acta Neuropathol, 124:273-283, plus supplemental material pp. 1-10.
Vigal, 2002, A review on SNP and other types of molecular markers and their use in animal genetics, Genet Sel Evol 34:275-305.
Walker, 1992, Strand displacement amplification—an isothermal, in vitro DNA amplification technique, Nucl Acids Res 20(7):1691-1696.
Westin 2000, Anchored multiplex amplification on a microelectronic chip array, Nat Biotech 18:199-204.
Wienholds, 2004, Target-selected gene inactivation in zebrafish, Meth Cell Biol 77:69-90.

* cited by examiner

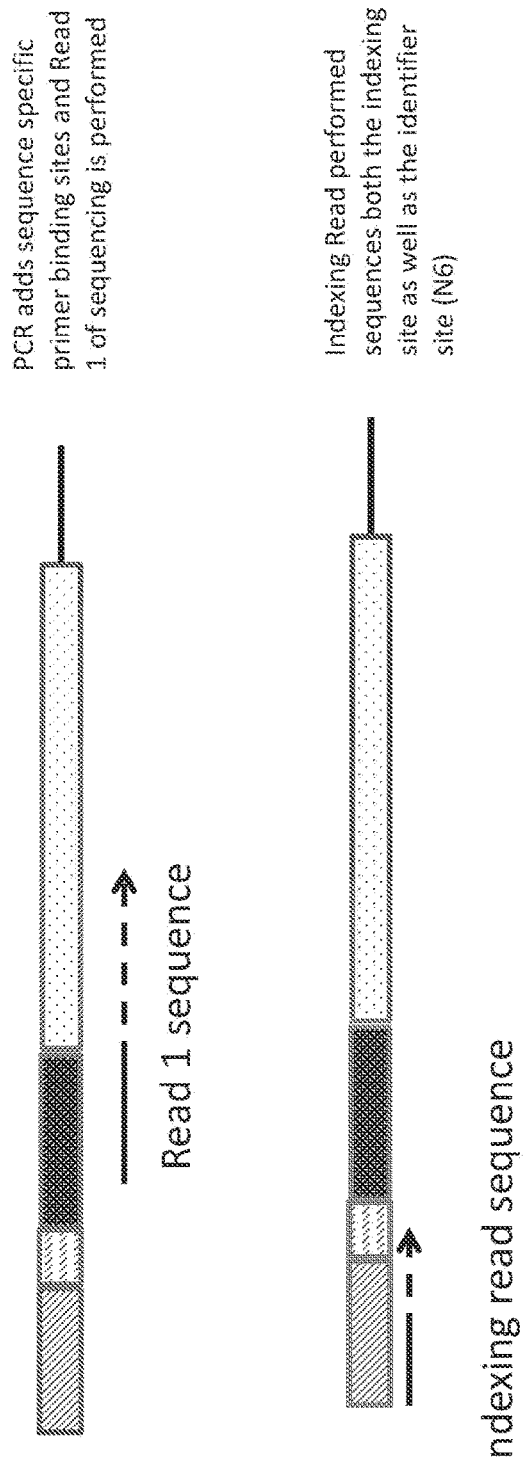

Example Adaptor

An adaptor sequence with necessary priming sites, the index site, and the identifier site CAGAGCACACGTCTGAACTCCAGTCACAGTGAGNNNNNNACACTTTCCCTACACGACGCTCTTCCGATCT (gDNA)

| Illumina flow cell plus indexing read priming site | Indexing site + Identifier site | Illumina forward sequencing read priming site |

Figure 3

Resolution of apparent duplicate reads by identifier sequence ligation

Libraries were generated from 100ng genomic DNA Covaris fragmented to ~500bp in length. These were enriched with the 344 gene cancer panel, ~12k probes covering 969kb of genomic space and sequenced on the ILMN Miseq. Different numbers of reads were randomly selected for this analysis

| Total reads randomly selected | Aligned read | Fold Target Coverage | Total duplicates after identifier analysis (true rate) | Percentage duplicates after identifier analysis (true rate) | Total apparent duplicates with no identifier | Percentage apparent duplicates with no identifier |
|---|---|---|---|---|---|---|
| 100K | 97,919 | 2X | 1854 | 1.89 | 3256 | 3.33 |
| 500K | 488,423 | 7X | 39731 | 8.13 | 68741 | 14.07 |
| 1M | 976,662 | 13X | 145589 | 14.91 | 237882 | 24.36 |
| 2M | 1,954,673 | 21X | 514848 | 26.34 | 764825 | 39.13 |
| 10M | 9,771,462 | 43X | 6493577 | 66.45 | 7515496 | 76.91 |

"Apparent" Duplicates – individual targets within libraries consist of one random end (result of fragmentation) and one common end (initiated with the sequence specific probe). Apparent duplicates are derived from sequencing libraries and using conventional measures of duplicate reads ie., reads were mapped using bowtie and all reads with the same start and end genomic coordinates were counted as duplicates.

"True" duplicates - An identifier sequence is introduced through ligation to differentiate between fragments of DNA that randomly have the same start and end mapping coordinates. The analysis method is described in the specification.

Figure 5

SEQUENCE LISTING

```
<160> NUMBER OF SEQ ID NOS: 9

<210> SEQ ID NO 1
<211> LENGTH: 70
<212> TYPE: DNA
<213> ORGANISM: artificial
<220> FEATURE:
<223> OTHER INFORMATION: Adaptor
<220> FEATURE:
<221> NAME/KEY: misc_feature
<222> LOCATION: (34)..(39)
<223> OTHER INFORMATION: n is a, c, g, or t

<400> SEQUENCE: 1
cagagcacac gtctgaactc cagtcacagt gagnnnnnna cactttccct acacgacgct      60
cttccgatct                                                            70

<210> SEQ ID NO 2
<211> LENGTH: 26
<212> TYPE: DNA
<213> ORGANISM: artificial
```

```
<220> FEATURE:
<223> OTHER INFORMATION: Priming site

<400> SEQUENCE: 2
agagcacacg tctgaactcc agtcac                                              26

<210> SEQ ID NO 3
<211> LENGTH: 29
<212> TYPE: DNA
<213> ORGANISM: artificial
<220> FEATURE:
<223> OTHER INFORMATION: forward priming site compliment

<400> SEQUENCE: 3
tctttcccta cacgacgctc ttccgatct                                           29

<210> SEQ ID NO 4
<211> LENGTH: 66
<212> TYPE: DNA
<213> ORGANISM: artificial
<220> FEATURE:
<223> OTHER INFORMATION: Forward adaptor
<220> FEATURE:
<221> NAME/KEY: misc_feature
<222> LOCATION: (59)..(66)
<223> OTHER INFORMATION: n is a, c, g, or t

<400> SEQUENCE: 4
aatgatacgg cgaccaccga gatctacact ctttccctac acgacgctct tccgatctnn         60 nnnnnn                                                                    66

<210> SEQ ID NO 5
<211> LENGTH: 72
<212> TYPE: DNA
<213> ORGANISM: artificial
<220> FEATURE:
<223> OTHER INFORMATION: Reverse adaptor
<220> FEATURE:
<221> NAME/KEY: misc_feature
<222> LOCATION: (65)..(72)
<223> OTHER INFORMATION: n is a, c, g, or t

<400> SEQUENCE: 5
caagcagaag acggcatacg agattccctt gtgactggag ttcagacgtg tgctcttccg         60
atctnnnnnn nn                                                             72

<210> SEQ ID NO 6
<211> LENGTH: 71
<212> TYPE: DNA
<213> ORGANISM: artificial
<220> FEATURE:
<223> OTHER INFORMATION: Reverse Adaptor
<220> FEATURE:
<221> NAME/KEY: misc_feature
<222> LOCATION: (64)..(71)
<223> OTHER INFORMATION: n is a, c, g, or t

<400> SEQUENCE: 6
caagcagaag acggcatacg agattgaagg gtgactggag ttcagacgtg tgctcttccg         60
atcnnnnnnn n                                                              71

<210> SEQ ID NO 7
<211> LENGTH: 21
<212> TYPE: DNA
<213> ORGANISM: artificial
<220> FEATURE:
```

```
<223> OTHER INFORMATION: Common partner
<220> FEATURE:
<221> NAME/KEY: misc_feature
<222> LOCATION: (1)..(8)
<223> OTHER INFORMATION: n is a, c, g, or t

<400> SEQUENCE: 7
nnnnnnnnag atcggaagag c                                              21

<210> SEQ ID NO 8
<211> LENGTH: 20
<212> TYPE: DNA
<213> ORGANISM: artificial
<220> FEATURE:
<223> OTHER INFORMATION: Primer

<400> SEQUENCE: 8
aatgatacgg cgaccaccga                                                20

<210> SEQ ID NO 9
<211> LENGTH: 21
<212> TYPE: DNA
<213> ORGANISM: artificial
<220> FEATURE:
<223> OTHER INFORMATION: Primer

<400> SEQUENCE: 9
caagcagaag acggcatacg a                                              21
```

COMPOSITIONS AND METHODS FOR IDENTIFICATION OF A DUPLICATE SEQUENCING READ

CROSS-REFERENCE

This application is a continuation of U.S. application Ser. No. 16/743,604, filed Jan. 15, 2020, which is a continuation of U.S. application Ser. No. 15/406,002, filed Jan. 13, 2017, which is a divisional of U.S. Ser. No. 14/540,917, filed Nov. 13, 2014, which claims the benefit of U.S. Provisional Application No. 61/903,826, filed Nov. 13, 2013, which are each herein incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NUGN-001-04US-SeqList-ST25.txt, date recorded: Jul. 21, 2021, file size 3 kilobytes).

FIELD OF THE PRESENT INVENTION

The present invention relates generally to the field of high throughput sequencing reactions and the ability to discern artifacts arising through sequence duplications from nucleotide molecules that are unique molecules.

BACKGROUND OF THE PRESENT INVENTION

In RNA sequencing applications, accurate gene expression measurements may be hampered by PCR duplicate artifacts that occur during library amplification. When analyzing RNA sequencing data, when two or more identical sequences are found, it can be difficult to know if these represent unique cDNA molecules derived independently from different RNA molecules, or if they are PCR duplicates derived from a single RNA molecule. In genotyping by sequencing, duplicate reads can be considered non-informative and may be collapsed down to a single read, thus reducing the number of sequencing reads used in final analysis. Generally, sequencing reads may be determined to be duplicates if both forward and reverse reads have identical starting positions, even though two independently generated molecules can have identical starting positions by random chance. Single primer extension based targeted re-sequencing suffers from an issue in that only one end of a sequencing read is randomly generated, while the other (reverse read) end is generated by a specific probe. This may make it difficult to determine if two reads are duplicates because they have been duplicated by PCR or because by chance they happened to start at the same position.

In expression analysis studies there may be limited value in doing paired end sequencing since the goal of the experiment is to determine amounts of transcript present as opposed to studying exon usage. In these studies, paired end sequencing adds costs while the only value is in helping distinguish PCR duplicates. The probability of two reads starting in the same position on only one end is higher than the probability of two reads having the same starting position on two ends (forward and reverse read). There is a need for improved methods that allow for low-cost, high throughput sequencing of regions of interest, genotyping or simple detection of RNA transcripts without inherent instrument inefficiencies that drive up sequencing costs due to the generation of unusable or non-desired data reads. The invention described herein fulfills this need. Here, we describe an adaptor approach that allows for the identification of true PCR duplicates and their removal.

The methods of the present invention provide novel methods for identifying true duplicate reads during sequencing, such as to improve data analysis of sequencing data, and other related advantages.

SUMMARY OF THE PRESENT INVENTION

The present invention is based, in part, on compositions and methods for discerning duplicate sequencing reads from a population of sequencing reads. The detection and/or removal of duplicate sequencing reads presented herein is a novel approach to increasing the efficacy of evaluating data generated from high throughput sequence reactions, including complex multiplex sequence reactions.

Accordingly, the present invention provides a method of detecting a duplicate sequencing read from a population of sample sequencing reads, the method comprising ligating an adaptor to a 5' end of each nucleic acid fragment of a plurality of nucleic acid fragments from one or more samples, wherein the adaptor comprises an indexing primer binding site, an indexing site, an identifier site, and a target sequence primer binding site. The ligated adaptor-nucleic acid fragment products can be amplified, thus generating a population of sequencing reads from the amplified adaptor-nucleic acid ligation products. The sequencing reads with a duplicate identifier site and target sequence can then be detected from the population of sequencing reads. The methods can further include the removal of the sequencing reads with the duplicate identifier site and target sequence from the population of sequence reads.

In some embodiments, the identifier site is sequenced with the indexing site or the target sequence. In further embodiments, the identifier site is sequenced separately from the indexing site or the target sequence.

In some embodiments, the adaptor comprises from 5' to 3' the indexing primer binding site; the indexing site; the identifier site; and the target sequence primer binding site. In further embodiments, the adaptor comprises from 5' to 3' the indexing primer binding site; the indexing site; the target sequence primer binding site; and the identifier site.

In some embodiments, the plurality of nucleic acid fragments is generated from more than one sample. In some embodiments, the nucleic acid fragments from each sample have the same indexing site. In some embodiments, the sequencing reads are separated based on the indexing site. In yet other embodiments, the separation of sequencing reads is performed prior to detecting sequence reads with a duplicate identifier site and target sequence.

In some embodiments, the nucleic acid fragments are DNA fragments, RNA fragments, or DNA/RNA fragments. In further embodiments, the nucleic acid fragments are genomic DNA fragments or cDNA fragments.

In some embodiments, the indexing site is between 2 and 8 nucleotides in length. In further embodiments, the indexing site is about 6 nucleotides in length. In some embodiments, the identifier site is between 1 and 8 nucleotides in length. In further embodiments, the identifier site is about 8 nucleotides in length.

In some embodiments, the indexing primer binding site is a universal indexing primer binding site; and in some embodiments, the target sequence primer binding site is a universal target sequence primer binding site.

The present invention also encompasses embodiments that include a kit comprising a plurality of adaptors, wherein each adaptor comprise an indexing primer binding site; an indexing site, and identifier site, and a target sequencing primer binding site.

BRIEF DESCRIPTION OF THE DRAWINGS

A better understanding of the novel features of the invention and advantages of the present invention will be obtained by reference to the following description that sets forth illustrative embodiments, in which the principles of the invention are utilized, and the accompanying drawings of which:

FIG. 2B is a continuation of FIG. 2A.

FIG. 3 offers a detailed view of the sequence of an example adaptor, among many envisioned embodiments, and the position of the indexing and identifier sites (SEQ ID NO: 1). "N" refers to any nucleic acid.

FIG. 5 depicts a data table demonstrating the accuracy of resolving true duplicates versus apparent or perceived duplicates using an identifier site in the adaptors.

DETAILED DESCRIPTION OF THE PRESENT INVENTION

Figure 1:
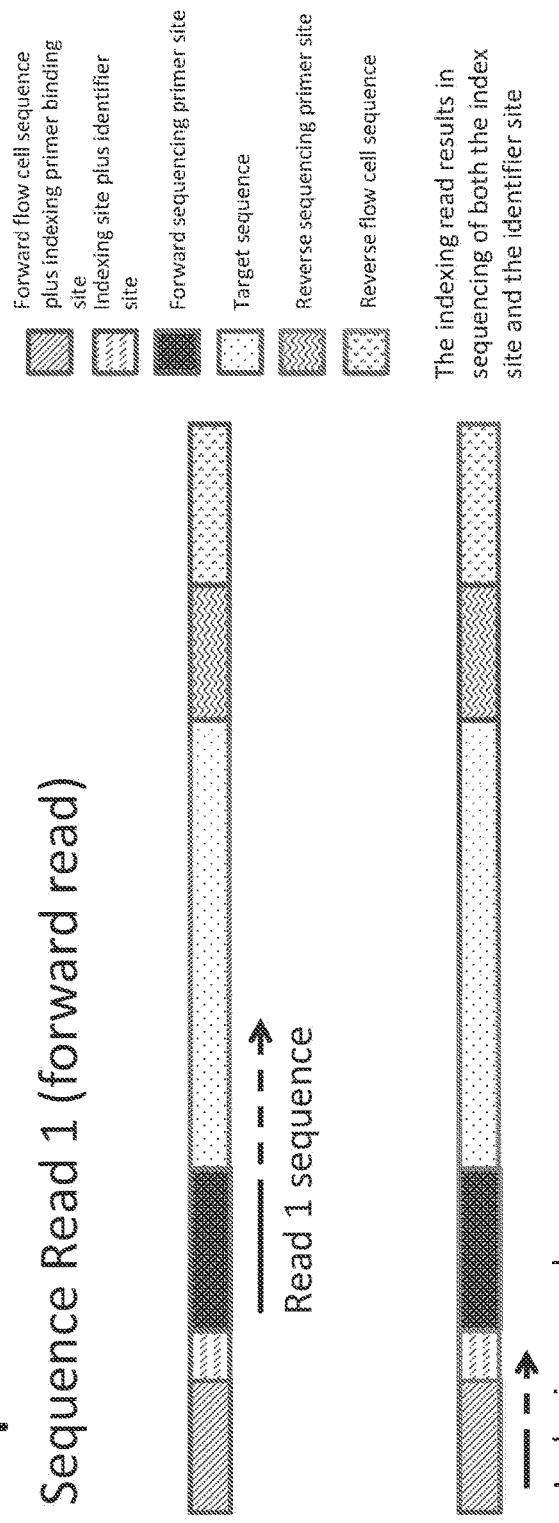
FIG. 1 depicts a schematic of generating sequencing reads of a library including where an indexing primer and a target sequence primer anneal.
Figure 2A:
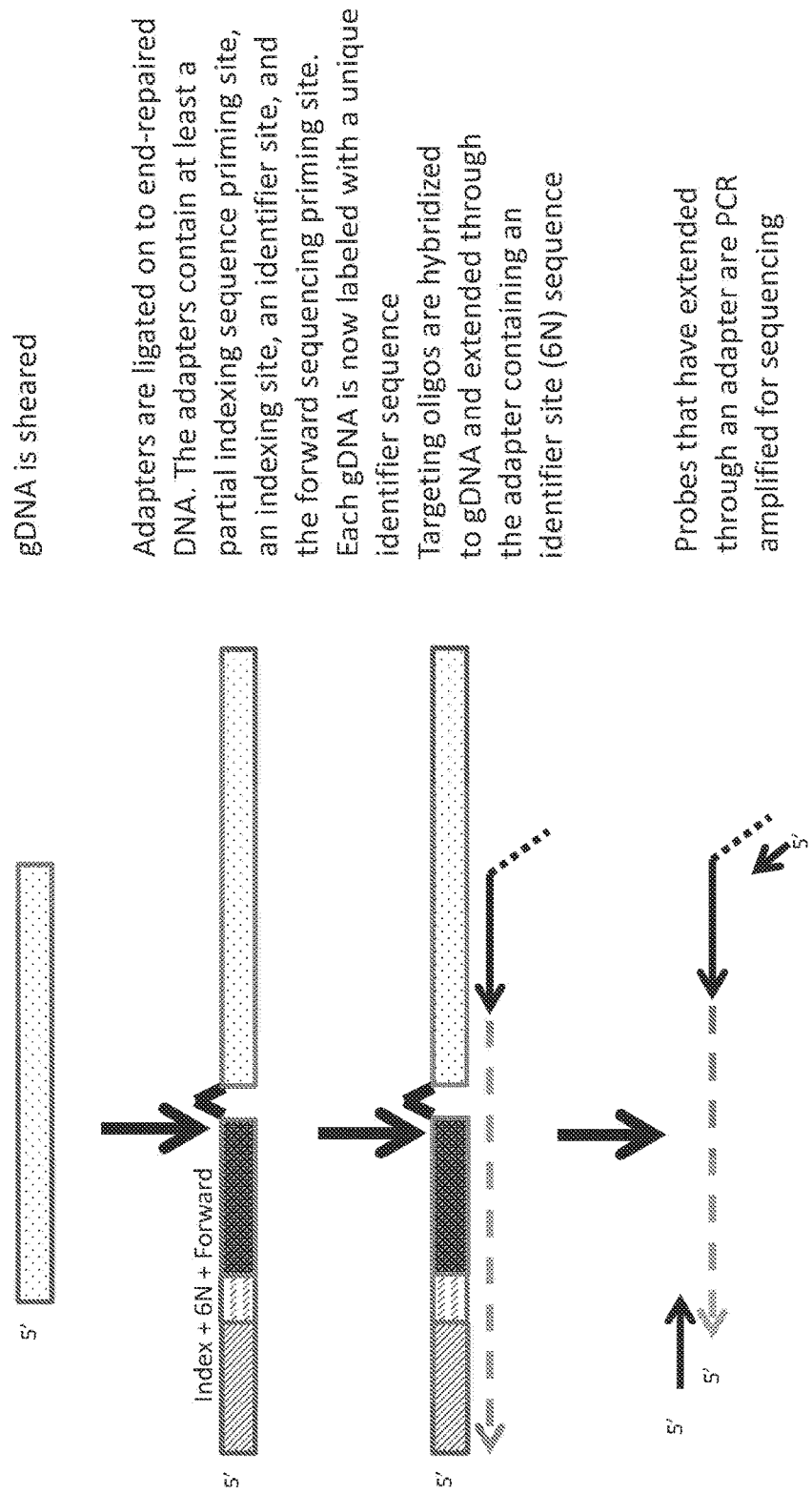
FIG. 2A depicts a mechanism of the Single Primer Enrichment Technology (SPET) and how an identifier site is carried over into the final library and how sequencing through the indexing site into the identifier site provides data on which nucleic acid molecule is being identified.
Figure 4:
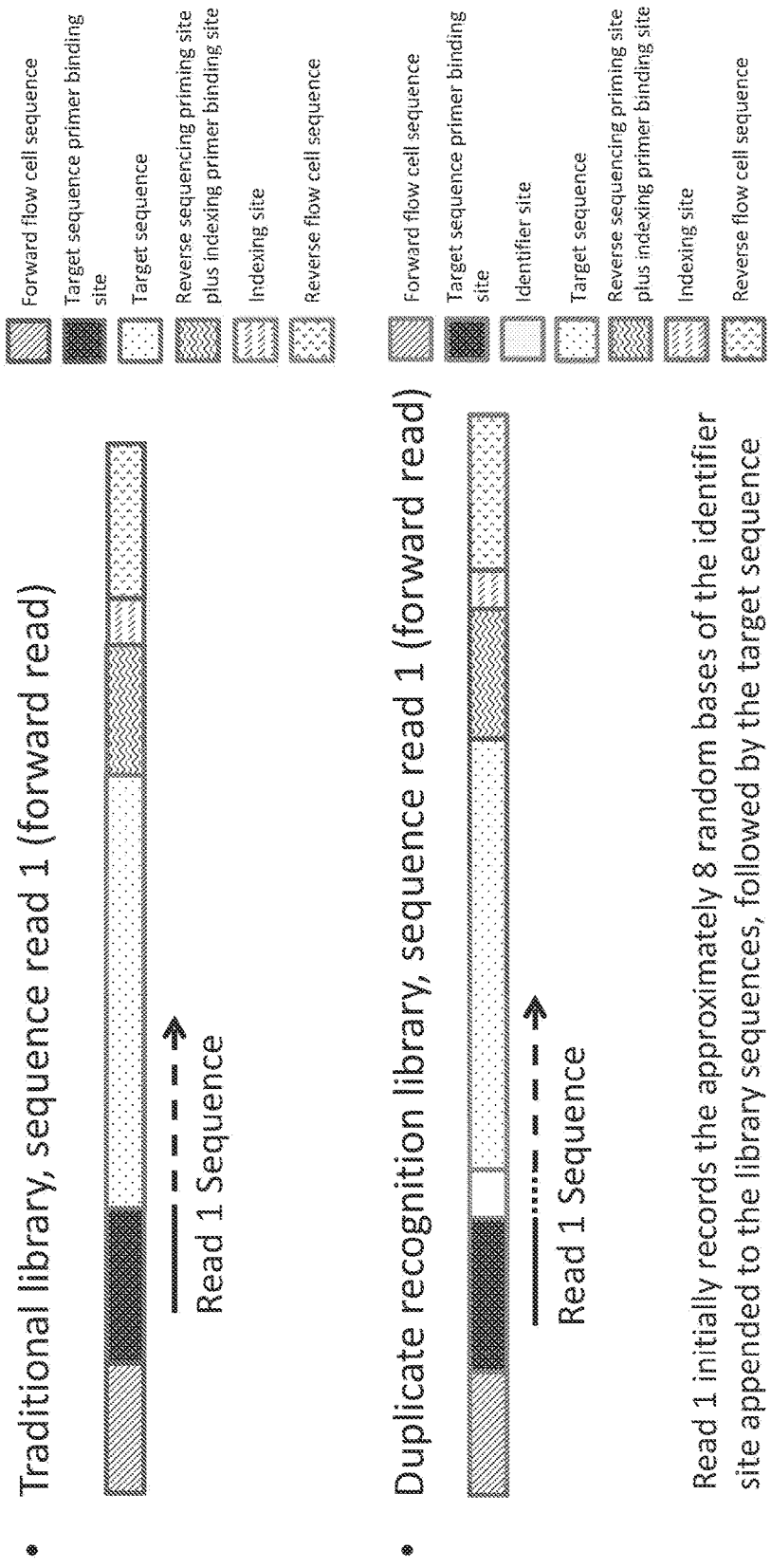
FIG. 4 depicts a schematic of two separate sequence libraries, indicating where the indexing primers and the target primers anneal in a traditional library as compared to a library using an identifier site.

The present invention is based, in part, on compositions and methods for discerning duplicate sequencing reads from a population of sequencing reads. The present invention encompasses methods of detecting sequences duplicated in sequencing applications, and further removal of the duplicated sequence reads. The present invention further encompasses kits comprising components that would allow for customized applications of the method of detecting and removing duplicated sequence reads in high throughput sequencing reactions. The compositions and methods can be used with various applications for genetic sample analysis, such as RNA sequence analysis, copy number variation analysis, methylation sequencing analysis, genotyping and whole genome amplification.

Reference will now be made in detail to exemplary embodiments of the invention. While the disclosed methods and compositions will be described in conjunction with the exemplary embodiments, it will be understood that these exemplary embodiments are not intended to limit the present invention. On the contrary, the present disclosure is intended to encompass alternatives, modifications and equivalents, which may be included in the spirit and scope of the present invention.

Unless otherwise specified, terms and symbols of genetics, molecular biology, biochemistry and nucleic acid used herein follow those of standard treatises and texts in the field, e.g. Kornberg and Baker, *DNA Replication*, Second Edition (W.H. Freeman, New York, 1992); Lehninger, *Biochemistry*, Second Edition (Worth Publishers, New York, 1975); Strachan and Read, Human *Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford,1984); and the like.

In some embodiments, the methods disclosed herein is for detecting from a population of sequencing reads a sequencing read, such as a duplicate sequencing read with a duplicate identifier site and target sequence. A duplicate sequencing read can be a sequencing read with the same identifier site and target sequence as another sequencing read in the population of sequencing reads.

Adaptor

The present invention provides compositions of adaptors and methods comprising use of an adaptor. An adapter refers to an oligonucleotide sequence, the ligation of which to a target polynucleotide or a target polynucleotide strand of interest enables the generation of amplification-ready products of the target polynucleotide or the target polynucleotide strand of interest. The target polynucleotide molecules may be fragmented or not prior to the addition of adaptors. In some embodiments, a method disclosed herein comprises ligating an adaptor to a 5' end of each nucleic acid fragment of a plurality of nucleic acid fragments from one or more samples.

Various adaptor designs are envisioned which are suitable for generation of amplification-ready products of target sequence regions/strands of interest. For example, the two strands of the adaptor may be self-complementary, non-complementary or partially complementary. In some embodiments, the adaptor can comprise an indexing primer binding site, an indexing site, an identifier site, and a target sequence primer binding site.

An indexing primer binding site is a nucleotide sequence for binding a primer for an indexing site. An indexing site is a nucleic acid sequence that acts as an index for multiple polynucleotide samples, thus allowing for the samples to be pooled together into a single sequencing run, which is known as multiplexing. In some embodiments, the indexing site is at least 2, 3, 4, 5, 6, 7, 8, 9, or 10 nucleotides in length. In some embodiments, the indexing site is between 2 and 8 nucleotides in length. In some embodiments, the indexing site is about 6 nucleotides in length.

An identifier site is a nucleic acid sequence that comprises random bases and is used to identify duplicate sequencing reads. In some embodiments, the identifier site is at least 2, 3, 4, 5, 6, 7, 8, 9, or 10 nucleotides in length. In some embodiments, the identifier site is between 1 and 8 nucleotides in length. In some embodiments, the identifier site is about 8 nucleotides in length. This identifier site can be designed as a set of sequences, or it can be semi-random, or it can be completely random. In addition, this identifier site can be a fixed length, or it can be a variable length. In some embodiments, the identifier sites in a plurality of adaptors are of a fixed length. For example, the identifier sites can all be eight random bases. In another embodiment, the identifier sites in a plurality of adaptors are of a variable length. For example, the identifier sites can range in size from 1 to 8 bases. In yet another embodiment, the identifier sites can be of a defined set of defined sequence. For example, the identifier site of a plurality of adaptors can be one of 96 defined six-base nucleotide sequences.

A target sequence primer binding site nucleotide sequence for binding a primer for a target sequence. The primer can be used to amplify the target sequence (e.g., a nucleic acid fragment from a sample). Accordingly, in some embodiments, the adaptor comprises an indexing primer binding site and a target sequence primer binding site.

A primer is a polynucleotide chain, typically less than 200 residues long, most typically between 15 and 100 nucleotides long, but can encompass longer polynucleotide chains. A primer targeting the primer binding sites are typically designed to hybridize to single-stranded nucleic acid strands. In some embodiments, the primers targeting the primer binding sites are designed to hybridize to single-stranded DNA targets. In the case where the sample comprises genomic DNA or other double-stranded DNA, the sample can be first denatured to render the target single stranded and enable hybridization of the primers to the desired sequence regions of interest. In these embodiments, the methods and compositions described herein can allow for region-specific enrichment and amplification of sequence regions of interest. In some embodiments, the other double-stranded DNA can be double-stranded cDNA generated by first and second strand synthesis of one or more target RNAs.

In other embodiments, the primers targeting the primer binding sites are designed to hybridize to double-stranded nucleic acid targets, without denaturation of the double stranded nucleic acids. In other embodiments, the primers targeting the primer binding sites are designed to hybridize to a double-stranded DNA target, without denaturation of the dsDNA. In these embodiments, the primers targeting the selected sequence regions of interest are designed to form a triple helix (triplex) at the selected sequence regions of interest. The hybridization of the primers to the double-stranded DNA sequence regions of interest can be carried out without prior denaturation of the double stranded nucleic acid sample. In such embodiments, the methods and compositions described herein can allow for region-specific enrichment as well as strand-specific enrichment and amplification of sequence regions of interest. This method can be useful for generation of copies of strand specific sequence regions of interest from complex nucleic acid without the need to denature the dsDNA input DNA, thus enabling enrichment and analysis of multiplicity of sequence regions of interest in the native complex nucleic acid sample. The method can find use for studies and analyses carried out in situ, enable studies and analysis of complex genomic DNA in single cells or collection of very small well defined cell population, as well as permit the analysis of complex genomic DNA without disruption of chromatin structures.

The primers of the invention are generally oligonucleotides that are employed in an extension reaction by a polymerase along a polynucleotide template, such as for amplification of a target sequence (e.g., in PCR). The oligonucleotide primer can be a synthetic polynucleotide that is single stranded, containing a sequence at its 3'-end that is capable of hybridizing with a sequence of the target polynucleotide. In some embodiments, the 3' region of the primer that hybridizes with the target nucleic acid has at least 80%, preferably 90%, more preferably 95%, most preferably 100%, complementarity to a primer binding site.

In some embodiments, the primer binding site is a binding site for a universal primer. A universal primer is a primer that can be used for amplifying a number of different sequences. In some embodiments, a universal primer is used to amplify different libraries. In some embodiments, an indexing primer binding site is a binding site for a universal indexing primer (i.e., the indexing primer binding site is a universal indexing primer binding site). In some embodiments, the adaptors used for ligating a plurality of nucleic acid fragments have a universal indexing primer binding site. In some embodiments, the universal indexing primer can be used to amplify and/or sequence a number of different indexing sites.

In some embodiments, a target sequence primer binding site is a binding site for a universal target sequence primer (i.e., the target sequence primer binding site is a universal target sequence primer binding site). In some embodiments, the adaptors used for ligating a plurality of nucleic acid fragments have a universal target sequence primer binding site. In some embodiments, the universal target sequence primer can be used to amplify and/or sequence a number of different target sequences.

In some embodiments, the adaptor comprises an identifier site 3' to an indexing site. In some embodiments, the adaptor comprises an identifier site 5' to an indexing site. In some embodiments, the adaptor comprises from 5' to 3' an indexing primer binding site, indexing site, identifier site, and target sequence primer binding site. In other embodiments, the adaptor comprises from 5' to 3' an indexing primer binding site, indexing site, identifier site, and target sequence primer binding site. In yet other embodiments, the adaptor comprises from 5' to 3' an indexing primer binding site, identifier site, indexing site, and target sequence primer binding site.

Samples

In some embodiments, an adaptor is ligated to a nucleic acid fragment (e.g., the 5' end of the nucleic acid fragment). The nucleic acid fragment can be from a plurality of nucleic acid fragments from one or more samples. The nucleic acid fragment can be RNA, DNA, or complex DNA, for example genomic DNA and PNA, in which case one might use a modified nucleic acid. The nucleic acid fragment may also be cDNA. The cDNA can be generated from RNA, e.g., mRNA.

The sample can be a biological sample. For example, the sample can be an animal, plant, bacterial, algal, or viral sample. In some embodiments, the sample is a human, rat, or mouse sample. The sample can be from a mixture of genomes of different species such as host-pathogen, bacterial populations and the like. The sample can be cDNA made from a mixture of genomes of different species. In some embodiments, the sample can be from a synthetic source. The sample can be mitochondrial DNA. The sample can be cell-free DNA. The cell-free DNA can be obtained from sources such as a serum or a plasma sample. The sample can comprise one or more chromosomes. For example, if the sample is from a human, the sample can comprise one or more of chromosome 1, 2, 3, 4, 5, 6, 7, 8, 9, 10, 11, 12, 13, 14, 15, 16, 17, 18, 19, 20, 21, 22, X, or Y. In some embodiments, the sample comprises a linear or circular genome. The sample can be plasmid DNA, cosmid DNA, bacterial artificial chromosome (BAC), or yeast artificial chromosome (YAC). The sample can be from more than one individual or organism. The sample can be double-stranded or single-stranded. The sample can be part of chromatin. The sample can be associated with histones.

In some embodiments, adaptors are ligated to a plurality of nucleic acid fragments from more than one sample, such as 2, 3, 4, 5, or more samples. In some embodiments, the nucleic acid fragments from each sample have the same indexing site. In some embodiments, a plurality of nucleic acid fragments is generated from a first sample and a second sample and adaptors are ligated to each nucleic acid fragment, in which adaptors ligated to each nucleic acid fragment from the first sample have the same first indexing site and adaptors ligated to nucleic acid fragments from the second sample has the same second indexing site. In some embodiments, the nucleic acid fragments or data associated with the nucleic acid fragments (e.g., sequencing reads) are separated based on the indexing site.

In some embodiments, a population of nucleic acid fragments generated from a sample is of one or more specific size range(s). In some embodiments, the fragments have an average length from about 10 to about 10,000 nucleotides. In some embodiments, the fragments have an average length from about 50 to about 2,000 nucleotides. In some embodiments, the fragments have an average length from about 100-2,500, 10-1,000, 10-800, 10-500, 50-500, 50-250, or 50-150 nucleotides. In some embodiments, the fragments have an average length less than 10,000 nucleotide, such as less than 5,000 nucleotides, less than 2,500 nucleotides, less than 2,500 nucleotides, less than 1,000 nucleotides, less than 500 nucleotides, such as less than 400 nucleotides, less than 300 nucleotides, less than 200 nucleotides, or less than 150 nucleotides.

In some embodiments, fragmentation of the nucleic acids can be achieved through methods known in the art. Fragmentation can be achieved through physical fragmentation methods and/or enzymatic fragmentation methods. Physical fragmentation methods can include nebulization, sonication, and/or hydrodynamic shearing. In some embodiments, the fragmentation can be accomplished mechanically comprising subjecting the nucleic acids in the input sample to acoustic sonication. In some embodiments, the fragmentation comprises treating the nucleic acids in the input sample with one or more enzymes under conditions suitable for the one or more enzymes to generate double-stranded nucleic acid breaks. Examples of enzymes useful in the generation of nucleic acid or polynucleotide fragments include sequence specific and non-sequence specific nucleases. Non-limiting examples of nucleases include DNase I, Fragmentase, restriction endonucleases, variants thereof, and combinations thereof. Reagents for carrying out enzymatic fragmentation reactions are commercially available (e.g., from New England Biolabs). For example, digestion with DNase I can induce random double-stranded breaks in DNA in the absence of $Mg^{++}$ and in the presence of $Mn^{++}$. In some embodiments, fragmentation comprises treating the nucleic acids in the input sample with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample polynucleotides leaves overhangs having a predictable sequence. In some embodiments, the method includes the step of size selecting the fragments via standard methods known in the art such as column purification or isolation from an agarose gel.

In some embodiments, fragmentation of the nucleic acids is followed by end repair of the nucleic acid fragments. End repair can include the generation of blunt ends, non-blunt ends (i.e sticky or cohesive ends), or single base overhangs such as the addition of a single dA nucleotide to the 3'-end of the nucleic acid fragments, by a polymerase lacking 3'-exonuclease activity. End repair can be performed using any number of enzymes and/or methods known in the art including, but not limited to, commercially available kits such as the Encore™ Ultra Low Input NGS Library System I. In some embodiments, end repair can be performed on double stranded DNA fragments to produce blunt ends wherein the double stranded DNA fragments contain 5' phosphates and 3' hydroxyls. In some embodiments, the double-stranded DNA fragments can be blunt-end polished (or "end-repaired") to produce DNA fragments having blunt ends, prior to being joined to adapters. Generation of the blunt ends on the double stranded fragments can be generated by the use of a single strand specific DNA exonuclease such as for example exonuclease 1, exonuclease 7 or a combination thereof to degrade overhanging single stranded ends of the double stranded products. Alternatively, the double stranded DNA fragments can be blunt ended by the use of a single stranded specific DNA endonuclease, for example, but not limited to, mung bean endonuclease or Si endonuclease. Alternatively, the double stranded products can be blunt ended by the use of a polymerase that comprises single stranded exonuclease activity such as for example T4 DNA polymerase, or any other polymerase comprising single stranded exonuclease activity or a combination thereof to degrade the overhanging single stranded ends of the double stranded products. In some cases, the polymerase comprising single stranded exonuclease activity can be incubated in a reaction mixture that does or does not comprise one or more dNTPs. In other cases, a combination of single stranded nucleic acid specific exonucleases and one or more polymerases can be used to blunt end the double stranded fragments generated by fragmenting the sample comprising nucleic acids. In still other cases, the nucleic acid fragments can be made blunt ended by filling in the overhanging single stranded ends of the double stranded fragments. For example, the fragments may be incubated with a polymerase such as T4 DNA polymerase or Klenow polymerase or a combination thereof in the presence of one or more dNTPs to fill in the single stranded portions of the double stranded fragments. Alternatively, the double stranded DNA fragments can be made blunt by a combination of a single stranded overhang degradation reaction using exonucleases and/or polymerases, and a fill-in reaction using one or more polymerases in the presence of one or more dNTPs.

U.S. Patent Publication Nos. 2013-0231253 A1 and 2014-0274729 A1 further describe methods of generating nucleic acid fragments, methods of modifying the fragments and analysis of the fragments, and are incorporated by reference in their entirety herein.

Ligation of Adaptors

Ligation of adaptors at the desired end of the sequence regions of interest (e.g., at the 5' or 3' end of a nucleic acid fragment generated form a sample) is suitable for carrying out the methods of the invention. Various ligation modalities are envisioned, dependent on the choice of nucleic acid, nucleic acid modifying enzymes and the resulting ligatable end of the nucleic acid. For example, when a blunt end product comprising the target region/sequence of interest is generated, blunt end ligation can be suitable. Alternatively, where the cleavage is carried out using a restriction enzyme of known sequence specificity, leading to the generation of cleavage sites with known sequence overhangs, suitable ends of the adaptors can be designed to enable hybridization of the adaptor to the cleavage site of the sequence region of interest and subsequent ligation. Ligation also refers to any joining of two nucleic acid molecules that results in a single nucleic acid sequence that can be further modified to obtain the sequence of the nucleic acids in question. Reagents and methods for efficient and rapid ligation of adaptors are commercially available, and are known in the art.

In some embodiments, the 5' and/or 3' end nucleotide sequences of fragmented nucleic acids are not modified or end-repaired prior to ligation with the adapter oligonucleotides of the present invention. For example, fragmentation by a restriction endonuclease can be used to leave a predictable overhang, followed by ligation with one or more adapter oligonucleotides comprising an overhang complementary to the predictable overhang on a nucleic acid fragment. In another example, cleavage by an enzyme that leaves a predictable blunt end can be followed by ligation of blunt-ended nucleic acid fragments to adapter oligonucleotides comprising a blunt end. In some embodiments, end repair can be followed by an addition of 1, 2, 3, 4, 5, 6, 7, 8, 9, 10, 11, 12, 13, 14, 15, 16, 17, 18, 19, 20 or more nucleotides, such as one or more adenine, one or more thymine, one or more guanine, or one or more cytosine, to produce an overhang. Nucleic acid fragments having an overhang can be joined to one or more adapter oligonucleotides having a complementary overhang, such as in a ligation reaction. For example, a single adenine can be added to the 3' ends of end-repaired DNA fragments using a template independent polymerase, followed by ligation to one or more adapters each having a thymine at a 3' end. In some embodiments, adapter oligonucleotides can be joined to blunt end double-stranded nucleic acid fragments which have been modified by extension of the 3' end with one or more nucleotides followed by 5' phosphorylation. In some cases, extension of the 3' end can be performed with a polymerase such as for example Klenow polymerase or any of the suitable polymerases provided herein, or by use of a terminal deoxynucleotide transferase, in the presence of one or more dNTPs in a suitable buffer containing magnesium. In some embodiments, nucleic acid fragments having blunt ends can be joined to one or more adapters comprising a blunt end. Phosphorylation of 5' ends of nucleic acid fragments can be performed for example with T4 polynucleotide kinase in a suitable buffer containing ATP and magnesium. The fragmented nucleic acid molecules may optionally be treated to dephosphorylate 5' ends or 3' ends, for example, by using enzymes known in the art, such as phosphatases.

In some embodiments, appending the adaptor to the nucleic acid fragments generated by methods described herein can be achieved using a ligation reaction or a priming reaction. In some embodiments, appendage of an adaptor to the nucleic acid fragments comprises ligation. In some embodiments, ligation of the adaptor to the nucleic acid fragments can be following end repair of the nucleic acid fragments. In another embodiment, the ligation of the adaptor to the nucleic acid fragments can be following generation of the nucleic acid fragments without end repair of the nucleic acid fragments. The adaptor can be any type of adaptor known in the art including, but not limited to, conventional duplex or double stranded adaptors in which the adaptor comprises two complementary strands. In some embodiments, the adaptor can be a double stranded DNA adaptor. In some embodiments, the adaptor can be an oligonucleotide of known sequence and, thus, allow generation and/or use of sequence specific primers for amplification and/or sequencing of any polynucleotides to which the adaptor is appended or attached. In some embodiments, the adaptor can be a conventional duplex adaptor, wherein the adaptor comprises sequence well known in the art. In a some embodiments, the adaptor can be appended to the nucleic acid fragments generated by the methods described herein in multiple orientations. In some embodiment, the methods described herein can involve the use of a duplex adaptor comprising double stranded DNA of known sequence that is blunt ended and can bind to the double stranded nucleic acid fragments generated by the methods described herein in one of two orientations. In some embodiments, the adaptor can be ligated to each of the nucleic acid fragments such that each of the nucleic acid fragments comprises the same adaptor. In other words, each of the nucleic acid fragments comprises a common adaptor. In another embodiment, an adaptor can be appended or ligated to a library of nucleic acid fragments generated by the methods described herein such that each nucleic acid fragment in the library of nucleic acid fragments comprises the adaptor ligated to one or both ends. In another embodiment, more than one adaptor can be appended or ligated to a library of nucleic acid fragments generated by the methods described herein. The multiple adaptors may occur adjacent to one another, spaced intermittently, or at opposite ends of the nucleic acid fragments. In some embodiments, the adaptor can be ligated or appended to the 5' and/or 3' ends of the nucleic acid fragments generated by the methods described herein. The adaptor can comprise two strands wherein each strand comprises a free 3' hydroxyl group but neither strand comprises a free 5' phosphate. In some embodiments, the free 3' hydroxyl group on each strand of the adaptor can be ligated to a free 5' phosphate present on either end of the nucleic acid fragments of the present invention. In this embodiment, the adaptor comprises a ligation strand and a non-ligation strand whereby the ligation strand can be ligated to the 5' phosphate on either end of the nucleic acid fragment while a nick or gap can be present between the non-ligation strand of the adaptor and the 3' hydroxyl on either end of the nucleic acid fragment. In some embodiments, the nick or gap can be filled in by performing a gap repair reaction. In some embodiments, the gap repair can be performed with a DNA dependent DNA polymerase with strand displacement activity. In some embodiments, the gap repair can be performed using a DNA-dependent DNA polymerase with weak or no strand displacement activity. In some embodiments, the ligation strand of the adaptor can serve as the template for the gap repair or fill-in reaction. The gap repair or fill-in reaction may comprise an extension reaction wherein the ligation strand of the adaptor serves as a template and leads to the generation of nucleic acid fragments with complementary termini or ends. In some embodiments, the gap repair can be performed using Taq DNA polymerase. In some embodiments, the ligation of the first adaptor to the nucleic acid fragments generated by the methods described herein may not be followed by gap repair. The nucleic acid fragments may comprise the adaptor sequence ligated only at the 5' end of each strand.

Ligation and, optionally gap repair, of the adaptor to the nucleic acid fragments generates an adaptor-nucleic acid fragment complex. In some embodiments, the adaptor-nucleic acid fragment complex can be denatured. Denaturation can be achieved using any of the methods known in the art including, but not limited to, physical, thermal, and/or chemical denaturation. In some embodiments, denaturation can be achieved using thermal or heat denaturation. In some embodiments, denaturation of the adaptor-nucleic acid fragment complex generates single stranded nucleic acid fragments comprising the adaptor sequence at only the 5'end of the nucleic acid fragments. In another embodiment, denaturation of the first adaptor-nucleic acid fragment complex generates single stranded nucleic acid fragments comprising adaptor sequence at both the 5'end and 3'end of the nucleic acid fragments.

Methods of Amplification

The methods, compositions and kits described herein can be useful to generate amplification-ready products directly from a nucleic acid source for downstream applications such as next generation sequencing, as well as generation of libraries with enriched population of sequence regions of interest. In some embodiments, the adapter-nucleic fragment ligated products, e.g., from the ligation of an adaptor to a 5' end of each nucleic acid fragment of a plurality of nucleic acid fragments from one or more samples, is amplified.

Methods of amplification are well known in the art. In some embodiments, the amplification is exponential, e.g. in the enzymatic amplification of specific double stranded sequences of DNA by a polymerase chain reaction (PCR). In other embodiments the amplification method is linear. In other embodiments the amplification method is isothermal. In some embodiments, the amplification is exponential, e.g. in the enzymatic amplification of specific double stranded sequences of DNA by a polymerase chain reaction (PCR).

Suitable amplification reactions can be exponential or isothermal and can include any DNA amplification reaction, including but not Limited to polymerase chain reaction (PCR), strand displacement amplification (SDA) linear amplification, multiple displacement amplification (MDA), rolling circle amplification (RCA), single primer isothermal amplification (SPIA, see e.g. U.S. Pat. No. 6,251,639), Ribo-SPIA, or a combination thereof. In some cases, the amplification methods for providing the template nucleic acid may be performed under limiting conditions such that only a few rounds of amplification (e.g., 2, 3, 4, 5, 6, 7, 8, 9, 10, 11, 12, 13, 14, 15, 16, 17, 18, 19, 20, 21, 22, 23, 2.4, 25, 26, 27, 28, 29, 30 etc.), such as for example as is commonly done for cDNA generation. The number of rounds of amplification can. be about 1-30, 1-20, 1-15, 1-10, 5-30, 10-30, 15-30, 20-30, 10-30, 15-30, 20-30, or 25-30.

PCR is an in vitro amplification procedure based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

LCR uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

SDA (Westin et a 2000, Nature Biotechnology, 18, 199-202; Walker et al 1992, Nucleic Acids Research, 20, 7, 1691-1696), is an isothermal amplification technique based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Some aspects of the invention utilize linear amplification of nucleic acids or polynucleotides. Linear amplification generally refers to a method that involves the formation of one or more copies of the complement of only one strand of a nucleic acid or polynucleotide molecule, usually a nucleic acid or polynucleotide analyte. Thus, the primary difference between linear amplification and exponential amplification is that in the latter process, the product serves as substrate for the formation of more product, whereas in the former process the starting sequence is the substrate for the formation of product but the product of the reaction, i.e. the replication of the starting template, is not a substrate for generation of products. In linear amplification the amount of product formed increases as a linear function of time as opposed to exponential amplification where the amount of product formed is an exponential function of time.

Downstream Applications

One aspect of the present invention is that the methods and compositions disclosed herein can be efficiently and cost-effectively utilized for downstream analyses, such as in next generation sequencing or hybridization platforms, with minimal loss of biological material of interest. The methods of the present invention can also be used in the analysis of genetic information of selective genomic regions of interest (e.g., analysis of SNPs or other disease markers) as well as genomic regions which may interact with the selective region of interest. The methods of the present invention may further be used in the analysis of copy number variation as well as differential expression.

Sequencing

In some embodiments, a population of sequencing reads is generated from the amplified adapter-nucleic fragment ligated products. In some embodiments, a sequencing read comprises an index read, which comprises the sequence of an indexing site. In some embodiments, an index read comprises the sequence of an indexing site and the sequence of an identifier site. For example, the indexing site is sequenced with the identifier site. In some embodiments, the index read does not include the sequence of an identifier site. For example, the indexing site is not sequenced with the identifier site. In some embodiments, a sequencing read comprises the target sequence. In some embodiments, a sequencing read comprises a target sequence and an identifier sequence. For example, the target sequence is sequenced with the identifier site. In some embodiments, the target sequence is not sequenced with the identifier site.

The methods of the present invention are useful for sequencing by the method commercialized by Illumina, as described U.S. Pat. Nos. 5,750,341; 6,306,597; and 5,969,119.

In general, double stranded fragment polynucleotides can be prepared by the methods of the present invention to produce amplified nucleic acid sequences tagged at one (e.g., (A)/(A') or both ends (e.g., (A)/(A') and (C)/(C')). In some cases, single stranded nucleic acid tagged at one or both ends is amplified by the methods of the present invention (e.g., by SPIA or linear PCR).The resulting nucleic acid is then denatured and the single-stranded amplified polynucleotides are randomly attached to the inside surface of flow-cell channels. Unlabeled nucleotides are added to initiate solid-phase bridge amplification to produce dense clusters of double-stranded DNA. To initiate the first base sequencing cycle, four labeled reversible terminators, primers, and DNA polymerase are added. After laser excitation, fluorescence from each cluster on the flow cell is imaged. The identity of the first base for each cluster is then recorded. Cycles of sequencing are performed to determine the fragment sequence one base at a time.

In some embodiments, the methods of the invention are useful for preparing target polynucleotides for sequencing by the sequencing by ligation methods commercialized by Applied Biosystems (e.g., SOLiD sequencing). In other embodiments, the methods are useful for preparing target polynucleotides for sequencing by synthesis using the methods commercialized by 454/Roche Life Sciences, including but not limited to the methods and apparatus described in Margulies et al., *Nature* (2005) 437:376-380 (2005); and U.S. Pat. Nos. 7,244,559; 7,335,762; 7,211,390; 7,244,567; 7,264,929; and 7,323,305. In other embodiments, the methods are useful for preparing target polynucleotide(s) for sequencing by the methods commercialized by Helios BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058. In other embodiments, the methods are useful for preparing target polynucleotide(s) for sequencing by the methods commercialized by Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764.

An example of a sequencing technique that can be used in the methods of the provided invention is semiconductor sequencing provided by Ion Torrent (e.g., using the Ion Personal Genome Machine (PGM)). Ion Torrent technology can use a semiconductor chip with multiple layers, e.g., a layer with micro-machined wells, an ion-sensitive layer, and an ion sensor layer. Nucleic acids can be introduced into the wells, e.g., a clonal population of single nucleic can be attached to a single head, and the bead can be introduced into a well. To initiate sequencing of the nucleic acids on the beads, one type of deoxyribonucleotide (e.g., dATP, dCTP, dGTP, or dTTP) can be introduced into the wells. When one or more nucleotides are incorporated by DNA polymerase, protons (hydrogen ions) are released in the well, which can be detected by the ion sensor. The semiconductor chip can then be washed and the process can be repeated with a different deoxyribonucleotide. A plurality of nucleic acids can be sequenced in the wells of a semiconductor chip. The semiconductor chip can comprise chemical-sensitive field effect transistor (chemFET) arrays to sequence DNA (for example, as described in U.S. Patent Application Publication No. 20090026082). Incorporation of one or more triphosphates into a new nucleic acid strand at the 3' end of the sequencing primer can be detected by a change in current by a chemFET. An array can have multiple chemFET sensors.

Another example of a sequencing technique that can be used in the methods of the provided invention is nanopore sequencing (see e.g., Soni G V and Meller A. (2007) *Clin Chem* 53: 1996-2001). A nanopore can be a small hole of the order of 1 nanometer in diameter. Immersion of a nanopore in a conducting fluid and application of a potential across it can result in a slight electrical current due to conduction of ions through the nanopore. The amount of current that flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore can represent a reading of the DNA sequence.

Data Analysis

In some embodiments, the sequence reads are used in the analysis of genetic information of selective genomic regions of interest as well as genomic regions which may interact with the selective region of interest. Amplification methods as disclosed herein can be used in the devices, kits, and methods known to the art for genetic analysis, such as, but not limited to those found in U.S. Pat. Nos. 6,449,562, 6,287,766, 7,361,468, 7,414,117, 6,225,109, and 6,110,709.

In some embodiments, the sequencing reads are used to detect duplicate sequencing reads. In some embodiments, a sequencing read is identified as a duplicate sequencing read when it contains an identifier site and target sequence that is the same as another sequencing read from the same population of sequencing reads.

In some embodiments, duplicate sequencing reads are differentiated from one another as being true duplicates versus apparent or perceived duplicates. Apparent or perceived duplicates may be identified from sequencing libraries and using conventional measures of duplicate reads (i.e., reads were mapped using bowtie), where all reads with the same start and end nucleic acid coordinates were counted as duplicates. True duplicates may be identified from sequencing libraries having had an identifier site introduced through ligation to differentiate between fragments of DNA that randomly have the same start and end mapping coordinates.

In some embodiments, the sequence of the identifier sites from the index read of two nucleic acids generated from any dsDNA may have the same start site, as determined from the sequencing reads of the target sequence of the generated nucleic acid fragments. If the identifier site from the index read of the two nucleic acid fragments are not identical, then the target sequence reads were not generated from the same original dsDNA molecule and, therefore, are no true duplicate reads. The ligation of random sequences onto dsDNA molecules, accompanied by the methods of the invention, allow for the identification of true duplicate reads versus apparent or perceived duplicate reads.

In some embodiments, the sequence of the identifier sites from the index read of two nucleic acid fragments generated from a genomic DNA (gDNA) molecule that have the same start site, which can be determined from the sequencing reads of the target sequence of the nucleic acid fragments is determined. If the identifier site from the index read of the two nucleic acid fragments are not identical, then the target sequence reads were not generated from the same original gDNA molecule and, therefore, are not true duplicate reads. In another embodiment, an identifier site is inserted at the adapter insert junction. The sequence of the identifier site is carried through the library amplification step. The identifier site is the first sequence read during the forward read. As the identifier sequence is not logically present adjacent to naturally occurring sequence, this uniquely identifies the DNA fragment. Therefore, by ligating random sequences onto the original gDNA, the methods of the invention identify true duplicate reads.

In some embodiments, a duplicate sequencing read is detected and analyzed. Duplicate reads can be filtered using 'samtools rmdup', wherein reads with identical external coordinates are removed, only one read with highest mapping quality is retained. After filtering, a filtered set of deduplicated reads can be used in any downstream analysis. Conversely, this filtering step can be skipped, and downstream analysis can be done using the unfiltered reads, including duplicates.

In some embodiments, sequencing reads are generated from a number of samples. In some embodiments, adaptors are ligated to a plurality of nucleic acid fragments from the samples, in which the nucleic acid fragments from each sample has the same indexing site. In some embodiments, a plurality of nucleic acid fragments is generated from a first sample and a second sample and adaptors are ligated to each nucleic acid fragment, in which adaptors ligated to each nucleic acid fragment from the first sample have the same first indexing site and adaptors ligated to nucleic acid fragments from the second sample has the same second indexing site. In some embodiments, the data associated with the nucleic acid fragments (e.g., sequencing reads) are separated based on the indexing site before sequencing reads of the target sequence and/or identifier site are analyzed. In some embodiments, the nucleic acid fragments or data associated with the nucleic acid fragments (e.g., sequencing reads) are separated based on the indexing site before duplicate sequencing reads are analyzed and/or removed.

In some embodiments, a method disclosed herein identifies or detects one or more true duplicate(s) with increased accuracy as compared to other methods. For example, in some embodiments, a method disclosed herein identify true duplicates (in contrast to identifying apparent or perceived duplicates) with increased accuracy as compared to other methods. The increased resolution and/or accuracy in identifying one or more true duplicate(s) can provide a considerable contribution to the state of the art in more accurately identifying true duplicates. In some embodiments, a method disclosed herein identifies or detects a true duplicate with increased efficiency as compared to other methods, such as paired end sequencing. The increase in accuracy, resolution, and/or efficiency in detecting duplicate reads (e.g., true duplicate(s)) can increase confidence in sequencing results, such as for expression and CNV analysis.

Kits

Any of the compositions described herein may be comprised in a kit. In a non-limiting example, the kit, in a suitable container, comprises: an adaptor or several adaptors, one or more of oligonucleotide primers and reagents for amplification.

The containers of the kits will generally include at least one vial, test tube, flask, bottle, syringe or other containers, into which a component may be placed, and preferably, suitably aliquotted. Where there is more than one component in the kit, the kit also will generally contain a second, third or other additional container into which the additional components may be separately placed. However, various combinations of components may be comprised in a container.

When the components of the kit are provided in one or more liquid solutions, the liquid solution can be an aqueous solution. However, the components of the kit may be provided as dried powder(s). When reagents and/or components are provided as a dry powder, the powder can be reconstituted by the addition of a suitable solvent.

A kit may include instructions for employing the kit components as well the use of any other reagent not included in the kit. Instructions may include variations that can be implemented.

In some embodiments, the invention provides kits containing any one or more of the elements disclosed in the above methods and compositions. In some embodiments, a kit comprises a composition of the invention, in one or more containers. In some embodiments, the invention provides kits comprising adapters, primers, and/or other oligonucleotides described herein. In some embodiments, the kit further comprises one or more of: (a) a DNA ligase, (b) a DNA-dependent DNA polymerase, (c) an RNA-dependent DNA polymerase, (d) a forward adapter (e) one or more oligonucleotides comprising reverse adaptor sequence and (f) one or more buffers suitable for one or more of the elements contained in said kit. The adapters, primers, other oligonucleotides, and reagents can be, without limitation, any of those described above. Elements of the kit can further be provided, without limitation, in any of the amounts and/or combinations (such as in the same kit or same container) described above. The kits may further comprise additional agents, such as those described above, for use according to the methods of the invention. For example, the kit can comprise a first forward adaptor that is a partial duplex adaptor as described herein, a second forward adapter, and a nucleic acid modifying enzyme specific for a restriction and/or cleavage site present in the first forward adaptor. The kit elements can be provided in any suitable container, including but not limited to test tubes, vials, flasks, bottles, ampules, syringes, or the like. The agents can be provided in a form that may be directly used in the methods of the invention, or in a form that requires preparation prior to use, such as in the reconstitution of lyophilized agents. Agents may be provided in aliquots for single-use or as stocks from which multiple uses, such as in a number of reaction, may be obtained.

In some embodiments, the kit comprises a plurality of adaptor oligonucleotides, wherein each of the adaptor oligonucleotides comprises at least one of a plurality of identifier site sequences, wherein each identifier site sequence of the plurality of identifier site sequences differs from every other identifier site sequence in said plurality of identifier site sequences at at least three nucleotide positions, and instructions for using the same. Adapters comprising different identifier site sequences can be supplied individually or in combination with one or more additional adapters having a different identifier site sequence. In some embodiments, the kit can comprises a plurality of adapter oligonucleotides.

EXAMPLES

Example 1

Identification of Duplicate Sequencing Reads with NuGEN Ovation Target Enrichment Library System Sample Description: 100 ng of DNA from a human HapMap sample (NA19238) was fragmented to approximately 500 base pair in length by sonication with a Covaris system (Covaris, Inc., Woburn, Mass.). The resulting DNA was treated with end repair enzyme mix NuGEN R01280 and R01439 (NuGEN Technologies, Inc., San Carlos, Calif.) according to supplier's recommendation to produce blunt ended DNA fragments.

Library Generation, Enrichment, and Identifier Site Incorporation: An oligonucleotide with segments, from 5' to 3' of the top strand, 1) an Illumina indexing read priming site such as AGAGCACACGTCTGAACTCCAGTCAC (SEQ ID NO:2), 2) an indexing site, 3) an identifier site having a random 6 base sequence and, 4) a sequence compatible with an Illumina forward sequencing priming site such as TCTTTCCCTACACGACGCTCTTCCGATCT (SEQ ID NO:3), was annealed to a second oligonucleotide to form a partially double stranded DNA adapter. Five uM of these adapters were ligated onto the end-repaired DNA using Ligase and Ligase reaction buffer from NuGEN's Ovation Ultralow Library System (NuGEN Technologies, Inc., San Carlos, Calif.) according to supplier's recommendations. Following 30 minutes of incubation at 25° C., the reaction mixture was diluted with water, 0.8× volume of Ampure XP magnetic beads (Agencourt Biosciences Corporation, A Beckman Coulter Company, Beverly, Mass.) was added and the solution thoroughly mixed. The beads were collected, washed and the ligated DNA fragments eluted according to manufacturer's recommendations. A pool of targeting probes was annealed to the eluted DNA fragments by initially heating the solution to 95° C. then slowly cooling the mixture from 80° C. to 60° C. by 0.6 degrees/minute.

Targeting probes that were specifically annealed were extended with Taq DNA polymerase (New England Biolabs, Inc., Ipswich, Mass.) according to the manufacturer's protocols. Following extension, the DNA fragments were collected on Agencourt magnetic beads, washed and eluted according to manufacturer's recommendations. These libraries were enriched by 30 cycles of PCR using NuGEN library enrichment primers (Ovation Target Enrichment Library System, NuGEN Technologies, Inc., San Carlos, Calif.) that also contain the Illumina flow cell sequences (Illumina Inc., San Diego, Calif.) according to supplier's recommendation.

The resulting libraries were quantitated by qPCR using a kit provided by KAPA, diluted to 2 nM and applied to an Illumina MiSeq DNA Sequencer (Illumina Inc., San Diego, Calif.). The following series was run: 36 base first read, 14 base second read, and 24 base third read. Data Analysis: The sequencer output was processed in accordance with manufacturer's recommendation. In order to analyze the data, the indexing read was split into two files. The first file contained the first 8 bases of the indexing reads and is utilized as the library index file for standard library parsing. The other file contains only the random bases and is set aside for further sequence parsing.

Following our data analysis pipeline of sequence alignment with bowtie aligner (Langmead B. et al., Ultrafast and memory-efficient alignment of short DNA sequences to the human genome. *Genome Biol.* 2009, 10:R2.), duplicate reads were identified by their genomic start positions. At this point, sequencing reads that started at the same genomic position were checked against the random bases file to see if they have the same or different set of random bases that were ligated to them. Where two sequences with the same starting genomic coordinate had the same set of random bases, they were considered to have come from the same initial DNA ligation event, regardless of which Ovation Target Enrichment targeting probe was used to generate the sequence fragment in question. These sequences, therefore, did not provide unique information about the starting genomic DNA and are considered as one sequencing read for the purpose of variant analysis. Two sequence reads with the same starting genomic coordinate that have different random bases were derived from unique ligation events and were considered to both be valid sequencing reads for the purpose of variant identification. FIG. 5 provides the analysis results demonstrating the identification of the duplicate reads. The use of an identifier site allowed for the determination of the number of true duplications versus the number of apparent or perceived duplicates.

If the sequences of two libraries are identical, their duplication status is unknown since this could occur by chance in any library. If an identifier sequence is used in combination with the library reads, the status can be determined (duplicates if identical, distinct if different). With the SPET system, one end is common so the probability of two libraries having identical ends increases. These would appear to be duplicate sequences and their true status can be determined by looking at an identifier sequence.

Over the sampling of all randomly selected reads, the use of identifier sites provided an increased resolution on the presence of true duplicates. When evaluating two million random reads, the apparent duplicates were found to comprise 39% of all reads. However, the true duplicates, identified through the use of an identifier site, were found to comprise only 26% of all reads. The methods employing the use of an identifier site were found to considerably increase the resolution of the true number of duplicates within the pool of reads.

Example 2

Removal of Duplicate Sequencing Reads with 8 Base Identifier Site

In a standard RNA sequencing library, adaptors are ligated to the ends of double stranded cDNA. These adaptors contain universal sequences that allow for PCR amplification and sequencing on high throughput sequencing machines. The adaptors are synthesized with a large population of additional sequences, in which each additional sequence is an identifier site, at the ligation end. The identifier sites are present at the junction between the adaptor and the cDNA. The sequence read starts with the identifier site and follows with the cDNA sequence.

This pool of identifier sites is used for the detection of PCR duplicates, as PCR duplicates will contain the identical identifier site, whereas two different cDNA molecules will ligate to two different adaptors containing two different identifier sites. This identifier site is designed as eight random bases introduced onto the end of the adaptor. Sequence reads from libraries made with such adaptors contain the 8 bases of the identifier site followed by the cDNA sequence. Standard PCR duplicate removal software such as PICARD, Markduplicates, and/or SAMtools rndup is used to identify and remove the PCR duplicates, leaving behind for analysis any instances of multiple cDNA fragments that happen to have the same sequence.

Example 3

Removal of Duplicate Sequencing Reads with Mixture of Random 1-8 Base Identifier Sites In a standard RNA sequencing library, adaptors are ligated to the ends of double stranded cDNA. These adaptors contain universal sequences that allow for PCR amplification and sequencing on high throughput sequencing machines. The adaptors are synthesized with a large population of additional sequences, in which each additional sequence is an identifier site, at the ligation end. The identifier sites are present at the junction between the adaptor and the cDNA. The sequence read starts with the identifier site and follows with the cDNA sequence.

This pool of identifier sites is used for the detection of PCR duplicates, as PCR duplicates will contain the identical identifier site, whereas two different cDNA molecules will ligate to two different adaptors containing two different identifier sites.

One to eight random bases are introduced onto the end of the adaptor. Sequence reads from libraries made with such adaptors contain between 1 and 8 bases of the identifier site followed by the cDNA sequence. Standard PCR duplicate removal software such as PICARD, Markduplicates, and/or SAMtools rndup is used to identify and remove the PCR duplicates, leaving behind for analysis any instances of multiple cDNA fragments that happen to have the same sequence.

Example 4

Removal of Duplicate Sequencing Reads with Mixture of 96 Defined 6-Base Identifier Sites In a standard RNA sequencing library, adaptors are ligated to the ends of double stranded cDNA. These adaptors contain universal sequences that allow for PCR amplification and sequencing on high throughput sequencing machines. The adaptors are synthesized with a large population of additional sequences, in which each additional sequence is an identifier site, at the ligation end. The identifier sites are present at the junction between the adaptor and the cDNA. The sequence read starts with the identifier site and follows with the cDNA sequence.

This pool of identifier sites is used for the detection of PCR duplicates, as PCR duplicates will contain the identical identifier site, whereas two different cDNA molecules will ligate to two different adaptors containing two different identifier sites.

A mixture of 96 defined six-bases sequences are introduced onto the end of the adaptors. Thus, each six-base sequence is an identifier site. Sequence reads from libraries made with such adaptors contain one of the 96 six-base identifier site followed by the cDNA sequence. Standard PCR duplicate removal software such as PICARD, Markduplicates, and/or SAMtools rndup is used to identify and remove the PCR duplicates, leaving behind for analysis any instances of multiple cDNA fragments that happen to have the same sequence.

Example 5

Identification of Duplicate Sequencing Reads in Determining mRNA Expression Levels Sample Description: Total RNA is extracted from tumor and normal adjacent tissue for the purpose of finding differences in expression levels of transcripts between the two sample types. 100 ng of each sample is converted into cDNA using the USP primers, reaction buffer, and Reverse Transcriptase provided in NuGEN's Encore Complete Library System (NuGEN Technologies, Inc., San Carlos, Calif.) according to the supplier's recommendations. This is followed by second strand synthesis, again using materials provided in the kit according to recommendations. Double stranded cDNA was prepared using the SuperScript® Double-Stranded cDNA Synthesis Kit from Life Technologies (Carlsbad, Calif.) according the manufacturer's instructions. DNA was sheared with a Covaris S-series device (Covaris, Inc., Woburn, Mass.) using the 200 bp sonication protocol provided with the instrument (10% duty cycle, 200 cycles/burst, 5 intensity, 180 seconds). DNA was treated with 1.5 uL 10× Blunting Buffer, 0.5 uL Blunting Enzyme (New England Biolabs, Inc., Ipswich, Mass.; p/n E1201) and 1.2 uL of 2.5 mM of each dNTP mix in a total volume of 15 uL for 30 minutes at 25° C. followed by 10 minutes at 70° C.

Library Generation: The DNA fragments were then subjected to end repair using end repair buffers and enzymes provided in NuGEN's Ovation Ultralow Library System (NuGEN Technologies, Inc., San Carlos, Calif.).

Forward adaptor
(SEQ ID NO: 4)
5' AATGATACGGCGACCACCGAGATCTACACTCTTTCCCTACACGACGC

TCTTCCGATCTNNNNNNNN,

Reverse adaptor 1)
(SEQ ID NO: 5)
5' CAAGCAGAAGACGGCATACGAGATTCCCTTGTGACTGGAGTTCAGAC

GTGTGCTCTTCCGATCTNNNNNNNN,

Reverse adaptor 2)
(SEQ ID NO: 6)
5' CAAGCAGAAGACGGCATACGAGATTGAAGGGTGACTGGAGTTCAGAC

GTGTGCTCTTCCGATCNNNNNNNN, and

Common partner 5' NNNNNNNNAGATCGGAAGAGC (SEQ ID NO:7) were all ordered from IDT (Integrated DNA Technologies, Coralville, Iowa). The reverse adaptors each contain a unique identifier (underlined) that enables libraries made with these adapters to be distinguished. In this case N represents an equimolar mixture of A, C, G, and T. A mixture of 5 uM forward, 5 uM reverse, and 10 uM common in 10 mM MgCl2, 50 mM Tris pH 8 was heated to 95C for 5 minutes, then cooled to 20 C. Adaptor ligation was performed by addition of 4.5 uL water, 3 uL Adaptor mix (prepared above), 6 uL 5× NEBNext Quick Ligation Reaction Buffer and 1.5 uL Quick T4 DNA Ligase (New England Biolabs, Inc., Ipswich, Mass.; p/n E6056), followed by incubation for 30 minutes at 25° C. followed by 10 minutes at 70° C. Ligation products were purified by adding 70 uL water and 80 uL of Ampure XP beads (Agencourt Genomics), washing twice with 70% ethanol and eluting with 20 uL of 10 mM Tris pH 8.0. Library products were amplified in a 50 uL PCR containing 0.5 uM each of primer (5' AATGATACGGCGACCACCGA (SEQ ID NO:8), and 5' CAAGCAGAAGACGGCATACGA (SEQ ID NO:9), 10 mM Tris-HCl, pH 8.3, 50 mM KCl, 2 mM MgCl2, 0.2 mM each dNTP, and 1 unit Taq polymerase. The reaction was cycled 15 times under the conditions 95 C for 15 seconds, 60 C for 1 minute. PCR products were purified with 1 volume of Ampure XP beads (Agencourt Biosciences Corporation, A Beckman Coulter Company, Beverly, Mass.) as described above. The library was analyzed by HS DNA Bioanalyzer (Agilent Technologies, Santa Clara, Calif.) and quantitated with the KAPA Library Quantification Kit (KAPA Biosystems, Wilmington, Mass.; p/n KK4835) according to the supplied instructions. The resulting libraries are combined and are compatible with standard TruSeq single end or paired Illumina sequencing protocols for GAIIx, MiSeq, or Hi Seq sequencing instruments (Illumina Inc., San Diego, Calif.). The following series is run; 50 base first read, 6 base second read. A third read is not required for counting purposes or duplication analysis.

Data Analysis: The sequencer output was processed in accordance with manufacturer's recommendation. The 6 bases of the index read is used for standard library parsing, separating the data files from the two sample types. The first 50 bases of the target sequence read are compared to each other. Any read that has identical sequence to any other read is identified as a duplicate and removed from the population, thus, only a single copy is retained within the file. Once the duplicate reads have been removed, 8 bases are trimmed from each read. The trimmed reads are aligned to a reference genome. Differential expression is then determined by comparing FPKM (fragments per kilobase per million reads) values between libraries utilizing scripts such as cufflinks or cuffdiff (Trapnell et al. 2010, Nature Biotechnology, 28, 511-515; Trapnell et al. 2013, Nature Biotechnology, 31, 46-53).

Example 6

Sequencing of the Identifier Site With the Target Sequence in Paired End Reads

The Ovation Library System for Low Complexity Samples (NuGEN Technologies, Inc., San Carlos, Calif.)

was used to generate four libraries, each from a single amplicon, following manufacturer's protocol. Purified libraries were mixed and sequenced as a multiplex on the Illumina MiSeq (Illumina Inc., San Diego, Calif.) to produce 125 nt forward, 8 nt index 1, 8 nt index 2, and 25 nt reverse reads. Because all amplicon reads start and end at the same sequence coordinates, the traditional method of marking library PCR duplicates (marking reads that start and end at the same genomic coordinates as duplicates) cannot be used. Instead, the 0-8nt of random sequence contained in the adaptors ligated to the amplicon were treated as an identifier sequence and used to mark duplicates. Any paired end reads that shared the same length and sequence of these random bases with any other paired end read was called a duplicate. The table below shows the results of this duplicate marking.

TABLE 1

| Library | Reads | Duplicate Reads | Reads from independent molecules |
|---------|--------|-----------------|----------------------------------|
| 1 | 454249 | 376797 | 77452 |
| 2 | 439367 | 364001 | 75366 |
| 3 | 317760 | 253057 | 64703 |
| 4 | 476572 | 398380 | 78192 |

Table 1 demonstrates the accuracy of the method used to differentiate between duplicate reads and reads from truly independent molecules. The population of reads from independent molecules, depicted in the final column of Table 1, represent sequences from independent amplicon molecules used in generating the libraries.

Example 7

Sequencing of the Identifier Site With the Target Sequence in Reduced Representation Bisulfite (RRBS) Libraries Reduced representation bisulfite (RRBS) libraries of the human genome are generated through the complete restriction enzyme digestion of 100 ng input sample, followed by selection for short fragments. The resulting pool of fragments are ligated to adaptor sequences comprising an indexing site and an identifier site. The identifier sites comprise either 6 or 8 random nucleotides. The sequences are then sequenced to identify the identifier sites, thus revealing the true number of duplicates in the pool. In the absence of identifier sites, the number of apparent or perceived duplicates are greater than the number of true duplicates. The inclusion of an identifier site results in the identification of the number of true duplicates, as compared to the larger number of apparent or perceived duplicates.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A method for detecting duplicate sequencing reads, the method comprising:
   obtaining amplicons each comprising an amplified fragment of a nucleic acid with an appended adaptor, wherein each adaptor comprises an identifier site comprising a plurality of nucleotides unique to the amplified fragment;
   sequencing the amplicons to generate sequence reads that include identifier and target sequences; and
   identifying sequence reads with identical identifier and target sequences as duplicates.

2. The method of claim 1, further comprising removing a duplicate read from the sequence reads.

3. The method of claim 1, wherein the identifier site is sequenced with the target sequence.

4. The method of claim 1, wherein the identifier site is sequenced separately from the target sequence.

5. The method of claim 1, wherein the amplicons include amplified fragments of cDNA.

6. The method of claim 1, wherein the amplicons include amplified fragments of genomic DNA.

7. The method of claim 1, wherein each adaptor includes a primer binding site.

8. The method of claim 7, wherein the primer binding site is a universal target sequencing primer binding site.

9. The method of claim 1, wherein each unique identifier is at least 6 nucleotides in length.

10. The method of claim 1, wherein the adaptors have been appended to the fragments using a ligation reaction or a priming reaction.

11. The method of claim 1, wherein each unique identifier is at a junction between the adapter and the nucleic fragment.

12. The method of claim 1, further comprising determining the genomic start position for each sequencing read.

13. The method of claim 1, wherein each adaptor further comprises an indexing site.

14. The method of claim 1, wherein each identifier site is at least 2, 3, 4, 5, 6, 7, 8, 9, or 10 nucleotides in length.

15. The method of claim 1, further comprising obtaining a sample comprising the nucleic acid, fragmenting the nucleic acid to yield the fragments of nucleic acid, appending the adaptors to the fragments of nucleic acid, and performing an amplification reaction to obtain the amplicons.

16. The method of claim 1, wherein the amplicons include amplified fragment of a nucleic acid from a first sample with an appended adaptor that includes a first index and amplified fragment of a nucleic acid from a second sample with an appended adaptor that includes a second index, and the method includes separating sequence reads by sample based on the first or second index.

* * * * *

Disclaimer

11,725,241 B2 - Douglas A. Amorese, Los Altos, CA (US); Jonathan Scolnick, San Francisco, CA (US); Ben Schroeder, San Mateo, CA (US). COMPOSITIONS AND METHODS FOR IDENTIFICATION OF A DUPLICATE SEQUENCING READ. Patent dated August 15, 2023. Disclaimer filed July 11, 2025, by the assignee, Tecan Genomics, Inc.

I hereby disclaim the entire term of said patent.

*(Official Gazette, August 26, 2025)*